(12) United States Patent
Naganuma

(10) Patent No.: US 7,691,073 B2
(45) Date of Patent: Apr. 6, 2010

(54) METHODS AND APPARATUSES FOR STIMULATING OTOLITH ORGANS BY LINEAR ACCELERATION

(76) Inventor: Hideaki Naganuma, 8-6-17-101, Tamagawagakuen, Machida-Shi, Tokyo (JP) 194-0041

( * ) Notice: Subject to any disclaimer, the term of this patent is extended or adjusted under 35 U.S.C. 154(b) by 1827 days.

(21) Appl. No.: 10/771,430

(22) Filed: Feb. 5, 2004

(65) Prior Publication Data

US 2004/0189079 A1 Sep. 30, 2004

(30) Foreign Application Priority Data

Mar. 31, 2003 (JP) ............................... 2003-096938

(51) Int. Cl.
*A61H 7/00* (2006.01)
(52) U.S. Cl. ............................. 601/98; 601/89; 601/90; 601/97
(58) Field of Classification Search .................. 601/98, 601/39, 53, 85, 90, 81, 97, 86, 87, 101, 23–38, 601/5; 297/31; 482/142, 143, 144; 472/135, 472/97, 119; 606/239–245, 247; 434/55, 434/307 R
See application file for complete search history.

(56) References Cited

U.S. PATENT DOCUMENTS

| 3,135,057 A | * | 6/1964 | Nelson et al. | 434/34 |
| 3,859,736 A | * | 1/1975 | Hill et al. | 434/55 |
| 4,019,727 A | * | 4/1977 | Martin et al. | 5/637 |
| 4,207,879 A | * | 6/1980 | Safadago et al. | 606/242 |
| 5,303,715 A | * | 4/1994 | Nashner et al. | 600/595 |
| 5,725,435 A | * | 3/1998 | De Castro Faria | 472/47 |
| 5,758,926 A | * | 6/1998 | Wilkie et al. | 297/423.19 |
| 5,941,839 A | * | 8/1999 | Ishikawa | 601/23 |
| 6,656,137 B1 | * | 12/2003 | Tyldsley et al. | 601/15 |
| 6,770,082 B2 | * | 8/2004 | Dominguez et al. | 606/130 |
| 6,796,947 B2 | * | 9/2004 | Watt et al. | 600/552 |
| 6,800,062 B2 | * | 10/2004 | Epley | 600/558 |

OTHER PUBLICATIONS

W. Precht: "The physiology of the vestibular nuclei. Part 1" In: Kormhuber HH, ed. Vestibular system. Berlin. Germany: Springer-Verlag. 1974: pp. 353-416, Handbook of sensory physiology: vol. 6.

(Continued)

*Primary Examiner*—Justine R Yu
*Assistant Examiner*—Arundipta Shome
(74) *Attorney, Agent, or Firm*—Young & Thompson

(57) ABSTRACT

A base section supports a revolution section. The revolution section supports a tilting section. The tilting section supports a seat section. The seat section includes a seat, a seat back and a step. The seat back has a restraining section. The restraining section includes an occipital region retainer and a temple retainer. Subject is seated with its occipital region and temples restrained by the restraining section. The head of subject is tilted on one side down from a head's horizontal plane in the Reid stereotaxic coordinate system to place one of left and right othlith organs within the head's horizontal plane. In this tilted position, different liner acceleration stimuli are applied to left and right otolith organs, respectively, for independent function tests of the left and right otolith organs.

9 Claims, 12 Drawing Sheets

OTHER PUBLICATIONS

Akito Fujino: "Complementary eye movements due to stimulation by sinusoidal linear acceleration—Eye reflex under otolith influence in normal humans vs., frequency characteristic and functional characteristic of otolith organs—" Ganjibi (Eye Ear Nose) 90: 335-347, 1987).

H.J. Scholtz: "Kompensatorische Augenbewegungen auf der parallelschwingenden Horizontalschaukel bei Gesunden und Vestibulariskranken" Z. Larying. Rhinol. 51: 46-57, 1972).

T.Futaki et al.: "Morphological study of otolitics of a guinea pig during parallel swing" Jibirinsho (Oto-rhino clinical practice) 75: Reprinting 5: 2468-2476, 1982.

M. Kitahara: "Acceleration registography—A new method of examination concerned with the labyrinthine righting reflex—" Ann Otol 74: 203-215, 1965.

S.G. Diamond et al.: "Binocular counterroling in humans during dynamic rotation" Acta Otolaryngol 87: 490-498, 1979.

C. Darlot et al.: "Eye movements induced by off-vertical axis rotation (OVAR) at small angles of tilt" Exp Brain res (1988) 73: pp. 91-105.

I. Koizuka et al.: "Nystagmus Responses in Normal Subjects during Eccentric Sinusoidal Rotation": Acta Octolaryngol (Stockh) 1994; Suppl. 501: pp. 34-37.

K. Nomura et al.: "New Otol Science Atlas-Morphology and Measure" pp. 176: Sanshodo Printing Co., Ltd., Japan.

H. Sasaki: "Otolith organs basic science and clinical practice" Oto-rhino clinical practice 60, Suppl. 2: 1970 pp. 73-123.

H. Naganuma et al.: "Three-dimensional analysis of morphological aspects of the human saccular macula", Ann Otol Rhinol Laryngol 110-2001, pp. 1017-1024.

R.H.I. Blanks et al.: "Planar relationships of the semicircular canals in man", Acta Otolaryngol 80: pp. 185-196m 1975.

S. G. Diamond et al.: Ocular Torsion as a Test of the Asymmetry Hypothesis of Space Motion Sickness, Acta Astronautica, vol. 27, pp. 11-17, 1992.

W. Precht: "The physiology of the vestibular nuclei. Part 1" In: Kormhuber HH, ed. Vestibular system. Berlin. Germany: Springer-Verlag. 1974: pp. 353-416, Handbook of sensory physiology: vol. 6.

S.G. Diamond et al.: "Binocular counterroling in humans during dynamic rotation" Acta Otolaryngol 87: 490-498, 1979.

C. Darlot et al.: "Eye movements induced by off-vertical axis rotation (OVAR) at small angles of tilt" Exp Brain res (1988) 73: pp. 91-105.

I. Koizuka et al.: "Nystagmus Responses in Normal Subjects during Eccentric Sinusoidal Rotation": Acta Octolaryngol (Stockh) 1994; Suppl. 501: pp. 34-37.

K. Nomura et al.: "New Otol Science Atlas-Morphology and Measure" pp. 176: Sanshodo Printing Co., Ltd., Japan Jul. 10, 1992.

* cited by examiner

METHODS AND APPARATUSES FOR STIMULATING OTOLITH ORGANS BY LINEAR ACCELERATION

FIELD OF THE INVENTION

The present invention relates to methods and apparatuses for stimulating a selected one of otolith organs, such as, utriculi (utricle) or sacculi (saccule), in human left and right ears by linear acceleration to enable a functional test of the selected utriculus or sacculus by measuring compensatory eye movements due to an eye reflex under otolith influence induced by the stimulation.

Otolith organs composed of utriculus and sacculus exist within each inner ear. In the specification, the expression "stimulating otolith organ, such as utriculus in left or right ear, primarily" is herein used to mean subjecting the otolith organ, such as utriculus in left or right ear, to linear acceleration.

BACKGROUND ART

A human ear may be divided into three sections, an outer ear including auricle and external auditory meatus, a middle ear including tympanic membrane, auditory ossicies and Eustachian tube, and an inner ear including cochlea and vestibule. The inner ear encodes physical stimuli from outside into electrical signals. Within the inner ear, vestibule responsible for balance exists as a separate section from cochlea that houses end organ of hearing. Within the vestibule, semicircular canals for sensing angular acceleration and otolith organs for sensing linear acceleration exist. The otolith organs of each inner ear are comprised of sacculus for sensing vertical linear acceleration and utriculus for sensing horizontal linear acceleration.

Within a temporal bone, the otolith organs coexist with the semicircular canals. Taking utriculus as an example, it is explained below how otolith organ contributes to sensing of linear acceleration.

Utriculus is a sac filled with a fluid called endolymph. Within the thickened bottom of walls defining the sac, hair cells are embedded as being surrounded by supporting cells and associated with nerve endings to form a macula called an utricular macula (macula utricule). The gelatinous material that overlies the macula is called the otolith membrane. It contains tiny crystalline particles of calcium carbonate, called otoliths (otoconia). The specific weight of the otoliths is greater than that of the endolymph.

Linear acceleration movement of the human head causes the hair cells to move together with the head, causing the otolith membrane to slide, due to the inertia, over the hair cells, bending the hairs. When the hair cells are bent toward the kinocilium, the hair cells depolarize and impulses sent to the brain increase in frequency. When the hair cells are bent in the opposite direction, the receptors hyperpolarize and impulse generation declines. As a result, the utricular maculae respond to changes in linear acceleration or velocity of head movement within the horizontal plane. Since the macula of the sacculus (macula saccule) is disposed on the side of the sac, the saccular maculae respond to changes in linear acceleration or velocity of head movement within the vertical plane.

The structure of a macula has a surface so that the utricular maculae and saccular maculae contribute effectively to sensing of linear acceleration of head movement in the tangential direction to the surfaces (W. Precht: "The physiology of the vestibular nuclei. Part 1" In: Kormhuber HH, ed. Vestibular system. Berlin. Germany: Springer-Verlag. 1974: pp 353-416, Handbook of sensory physiology: vol 6). Accordingly, the total four maculae consisting of two on the left side of a human head and the other two on the right side contribute to sensing the tilted position of the head on the recognition of the gravity's direction (vertical linear acceleration).

A great number of researches have been reported on otolith stimulation for an improved functional test of otolith organs. Representative examples of various proposals derived from the researches are an otolith stimulation by linear acceleration, an otolith stimulation during parallel swing, an otolith simulation by tilting the support surface, an otolith stimulation during dynamic rotation to induce binocular counterrolling, an otolith stimulation during off-vertical axis rotation, and an otolith stimulation during eccentric rotation. These stimulation methods are briefly described below.

(1) Otolith Stimulation by Linear Acceleration:

It is reported that sinusoidal linear acceleration of the head movement to the left or right stimulated the utriculus maculae in left and right ears to induce horizontal compensatory eye movements (Akito FUJINO: "Complementary eye movements due to stimulation by sinusoidal linear acceleration—Eye reflex under otolith influence in normal humans vs., frequency characteristic and functional characteristic of otolith organs—"Ganjibi (Eye Ear Nose) 90: 335-347, 1987). As the left and right utriculus maculae are simultaneously stimulated by linear acceleration, this method is inappropriate for subjecting them to different stimuli.

(2) Otolith Stimulation During Parallel Swing:

The parallel swing can give sufficiently great movements of a subject within the horizontal plane with small movements within the vertical plane. A trial is reported to determine the function of otolith organs by stimulating humans and animals during the parallel swing in the direction of axon (head-to-tail) and/or from side to side (H. J. Scholtz: "Kompensatorische Augenbewegungen auf der parallelschwingenden Horizontalschaukel bei Gesunden und Vestibulariskranken" Z. Larying. Rhinol. 51: 46-57, 1972). As the utricular maculae and saccular maculae in the left and right ears are simultaneously subjected to liner acceleration, this method is inappropriate for subjecting them to different stimuli.

FUTAKI et. al. (Takashi FUTAKI & Isuzu KAWABATA: "Morphological study of otolitics of a guinea pig during parallel swing" Jibirinsho (Oto-rhino clinical practice) 75: Reprinting 5: 2468-2476, 1982) discloses measuring eye movements of a guinea pig with its head set in right position during swing over 45 degrees in head-to-foot direction. The utricular maculae of both ears are simultaneously stimulated during the parallel swing. Accordingly, it is not considered that this method is appropriate for subjecting the utricular maculae to different stimuli.

(3) Otolith Stimulation by Tilting the Support Surface:

For examination of the reflex of labyrinth (labyrinthine righting reflex) and the reflex of neck (righting neck reflex) to enable a human to maintain the equilibrium, this stimulation method is proposed. As the head is tilted to stimulate the otolith organs for investigation of labyrinthine righting reflex, this method is inappropriate for subjecting the left and right utricular maculae to different stimuli (Masaaki KITAHARA: "Acceleration registography—A new method of examination concerned with the labyrinthine righting reflex—"Ann Otol 74: 203-215, 1965).

(4) Otolith Stimulation During Dynamic Rotation to Induce Binocular Counterrolling:

This stimulation method, by which binocular counterrolling is measured during dynamic rotation of the subject with the head tilted, stimulates the saccular maculae or the urticular maculae simultaneously (Shireley G. DIAMOND et. al.: "Binocular counterroling in humans during dynamic rotation" Acta Otolaryngol 87: 490-498, 1979). As the utricular maculae are simultaneously stimulated, this method is inappropriate for subjecting the utricular maculae to different stimuli.

(5) Otolith Stimulation During Off-vertical Axis Rotation (Off-vertical Axis Rotation; OVAR):

Included in this category are two methods, namely, a "rotation then tilt method" that tilts an axis of a chair, with respect to the direction of the gravity, after a stable state of the rotation about the axis has been established, and a "tilt then rotation method" that tilts the axis of the chair before the chair is driven to rotate. In either stimulation method, as the direction of the gravitational force applied to the head of the subject varies with different angular positions of the chain, the otolith organs are stimulated to induce eye movements due to otolith-eye reflex. As will be noted, these methods simultaneously stimulate the utricular and succular maculae within the both ears in a similar manner to the various stimulation methods discussed above (C. DARLOT, P. DENISE, J. DROULEZ, B. COHEN, AND A. BERTHOZ: "Eye movements induced by off-vertical axis rotation (OVAR) at small angles of tilt" Exp Brain Res (1988) 73: pp 91-105).

(6) Otolith Stimulation During Eccentric Rotation:

To stimulate the vestibule, a subject is placed on the axis of rotation (earth vertical axis: EVA) of a chair with the horizontal semicircular canals held within the horizontal plane parallel to the surface of earth to achieve rotation for observation of the vestibular-ocular reflex (VOR) gain in the concentric position. In the concentric position, the eye movements induced by the semicircular canals-ocular reflex occur. When the subject is placed off from the axis of rotation to achieve eccentric rotation, the subject receives not only angular acceleration forces, but also linear acceleration forces (tangential and normal acceleration forces). Under this condition, the otolith organs and the semicircular canals are simultaneously stimulated to give the total eye movements resulting from adding the eye movements induced by the otolith-ocular reflex to the eye movements induced by the semicircular canals-ocular reflex. The otolith function can be recognized by comparing the eye movements observed in the concentric position to the eye movements observed in the eccentric position. According to this stimulation method, however, the semicircular canals and the otolith organs of both ears are simultaneously stimulated (Izumi KOIZUKA, Noriak-i TAKEDA, Shinji SATO, Takeshi KUBO & Toru MATSUNAGA: "Nystagmus Responses in Normal Subjects during Eccentric Sinusoidal Rotation": Acta Octolaryngol (Stockh) 1993; Suppl. 501: pp 34-37).

As, with the previously listed systems, failure to achieve applying left and right utricular or saccular maculae with different stimuli makes individual functional tests impossible, the difficulty to accomplish the desired accuracy of the individual functional tests remains. If a system for applying the maculae with different stimuli were developed, the accuracy of the individual functional tests of the otolith organs would be enhanced, making a great advancement in this field of the medical treatment. Regrettably, there is no report on development of such system.

The inventor of the present invention has been involved in the functional test and study for many years. To the best knowledge of the inventor, there is no report on the significant progress in three-dimensional analysis of morphological aspects of the human otolith organs in the basic morphological study of the human otolith organs. Accordingly, as shown in FIG. 1(A), the recognition that the maculae of saccule and utricule are oriented vertically and horizontally, respectively, remains as the common knowledge (Kyoya. NOMURA, Fumihiko HIRAIDE & Takehiro HARADA: "New Otol Science Atlas-Morphology and Measure" pp 176: Sanshodo Printing Co., Ltd., Japan).

Among reports on the morphology of human otolith organs, Hiroshi SASAKI reported on the relationship, with respect to the a German horizontal plane (a flat plane containing the upper ends of external auditory meattus and the infraorbital region) and the sagittal plane, of three planes, namely, a major plane, a front plane and a rear plane, which the saccular macula was said to be composed of The utricular macula was said to be composed of three plane, namely, a front plane, a major plane and an inner plane. He reported that the front side of the major plane was lifted about 12° from the German plane and oriented inwardly about 90° from the sagittal plane, and the outer side of the major plane is lowered about 10° from the German plane (Hiroshi SASAKI: "Otolith organs basic science and clinical practice" Oto-rhino clinical practice 60, Suppl. 2: 1970 pp 73-123).

Over recent years, the inventor was devoting himself to the study of precise three-dimensional analysis of human otolith organs, more particularly, morphological aspects of succular macula, and reported the results in the year of 2001. In this report, a reference plane in the Reid stereotaxic coordinate system was determined by calculation. Using this calculated reference plane, each of multiple elements of the saccular macula (the multiple elements being several hundreds of microtriangular planes resulting from dividing the saccular macula) was evaluated in terms of its angular relationship with respect to the anterior-posterior, the left-right, and superior-inferior axes of the human skull. The results of the report demonstrated that the overall surface contour of the saccular macula was (not composed of flat planes) a curved surface forming a part of the surface of an ellipsoid (Hideaki NAGANUMA, Koji TOKUMASU, Makito OKAMOTO, Shinichiro HASHIMOTO, and Shohei YAMASHINA: "Three-dimensional analysis of morphological aspects of the human saccular macula", Ann Otol Rhinol Laryngol 110-2001, pp 1017-1024).

Using the same three-dimensional analysis as that used for the saccular macula, the inventor was devoting himself to the study of the human utircular macula over long years. As a result, it was made clear that the overall surface contour of the human utricular macula was not composed of flat planes, but a curved surface forming a part of the surface of an ellipsoid. It was also made clear that the exterior side of the utricular macula is tilted down about 10° from the horizontal plane (a flat plane containing three points including the upper ends of external auditory meattus and the infraorbital region) of the skull in the Reid stereotaxic coordinate system [see FIG. 1(B)]. This result confirmed the report by SASAKI (Hiroshi SASAKI: "Otolith organs basic science and clinical practice" Oto-rhino clinical practice 60, Suppl. 2: 1970 pp 73-123).

From the preceding three-dimensional analysis, it is now apparent that the exterior side of the utricular macula is tilted down about 10° from the horizontal plane (a flat plane containing three points including the upper ends of external auditory meattus and the infraorbital region) of the skull in the Reid stereotaxic coordinate system [R. H. I. BLANKS, I. S. CURTHOYS and H. MARKHAM, "Planar relationships of the semicircular canals in man", Acta Otolaryngol 80: pp 185-196 m 1975].

DISCLOSURE OF THE INVENTION

On the anatomical (three-dimensional) morphological analysis based on the above-mentioned knowledge, the present invention has been completed, making it possible to stimulate primarily a selected one of the utriculi of the human otolith organs within the ears. Specifically, when a subject is placed with the left ear, for example, tilted down 10°, the utricular macula within the right ear lies almost in a plane parallel to a head's horizontal plane in the Reid stereotaxic coordinate system, and the utricular macula within the left ear is tilted down 20° from the horizontal plane [see FIG. 1(C)] as different from the conventional head position of the subject at which, if a linear acceleration is applied from the left to right ears, the utricular maculae within the both ears are simultaneously stimulated.

In the above-mentioned head position tilted left ear down 10 degrees, when linear acceleration is applied to the head within the horizontal plane in a left-right direction, different stimuli will be applied to the utricular maculae within right and left ears, respectively, because different acceleration components are applied to the otolith membranes of the utricular maculae with the tangential planes, respectively. The individual functions of the utriculi can be measured by accurately measuring eye movements in one head position tilted right ear down 10 degrees, in another head position tilted left ear down. 10 degrees and in further head position with left and right ears within the horizontal plane.

As different stimuli can be applied to the left and right utricula maculae, respectively, a method and an apparatus for stimulating the otolith organs by linear acceleration according to the present invention are quite different from the conventional ones and may be ranked as epoch-making ones.

A main object of the present invention is to provide a method and an apparatus for stimulating left and right utriculi or sacculi by applying different stimuli to them, respectively, for individual functional tests of human left and right otolith organs.

A further object of the present invention is to provide a method and an apparatus for stimulating left and right utriculi or sacculi by applying different stimuli to them, respectively, without any difficulty and requiring any measuring skill of a high order for individual functional tests of human left and right otolith organs.

A still further object of the present invention is to provide a method and an apparatus for stimulating left and right utriculi or sacculi, which permit a practitioner to carry out an accurate measurement and functional test of a subject by restraining the subject firmly to the stimulating apparatus without making the subject uneasy and relaxed during the test.

Another object of the present invention is to provide a method and an apparatus for stimulating otolith organs, which allows for vestibular evoked myogenic potentials (VEMP) testing in addition to the preceding compensatory eye movements testing against varying subjects with different utricular and saccular maculae in orientation within the heads.

Still another object of the present invention is to provide a method and an apparatus for stimulating otolith organs, which can place a subject to any desired position to meet an objective of functional test.

A further object of the present invention is to provide an apparatus for stimulating otolith organs, which apparatus includes a major portion composed of a base section with a source of linear acceleration, a revolving section supported by the base section for linear reciprocal movements, a tilting section supported by the revolving section to tilt from the head horizontal plane in the Reid stereotaxic coordinate system, a seat section supported by the tilt section, and a restraining section on the seat section, which sections take to pieces easily, making it easy to maintain and overhaul.

The above-mentioned various objects and other features of the present invention are accomplished by a method and an apparatus for stimulating otolith organs, which are concretely described below.

According to one exemplary implementation of the present invention, in the field of apparatuses for stimulating otolith organs to cause complementary eye movements, there is provided an apparatus for stimulating otolith organs by linear acceleration, comprising a major portion composed of a base section with a source of linear acceleration, a revolving section supported by the base section for linear reciprocal movements, a tilting section supported by the revolving section to tilt from the head's horizontal plane in the Reid stereotaxic coordinate system, a seat section supported by the tilting section, and a restraining section, on the seat section, adjustable in all directions to restrain a subject with respect to the seat section.

The stimulating apparatus is provided, in which the revolving section is capable of adjustably turning a subject to any desired one of angular positions over 360 degrees, the restraining section includes a shoulder restrainer for restraining shoulders of the subject, an occipital region restrainer for restraining an occipital region of the subject, and a temple restrainer for restraining a temple region of the subject in order to firmly restrain a head portion of the subject during functional testing. The stimulating apparatus is provided, in which said base section is constructed as an unit form by including a major cover, the major cover being formed with guide grooves at a top thereof, the major cover including, inside thereof, a reciprocal mechanism that performs linear reciprocal movements caused due to the source of linear acceleration, the reciprocal mechanism including slides guided by said guide grooves.

The stimulating apparatus is provided, in which the revolving section includes a strut fixed to the base section and a frame supported, via a rotary mechanism, for revolution about the strut, the revolution of the frame is operable from outside of the frame in locking or unlocking position at any desired angular position during measurement to meet purpose of functional testing. The stimulating apparatus is provided, in which the revolving section includes a rotary main shaft, a pair of transmission gearing mechanisms cooperating with the main shaft via gear mount plates, a handle for operating the transmission gearing mechanisms, and means for rotating the main shaft via the transmission gearing mechanisms to a desired angular position using the handle in locking or unlocking position at the desired angular position.

The stimulating apparatus is provided, in which the seat section includes seat frames, seat back frames rotatably connected to the seat frames at one ends thereof, step supporting frames rotatably connected to the seat frames at the other ends thereof, the seat back frames and the seat frames are interlinked, and a vertical shaft fixedly supported on the seat frames, and guide metal fittings mounted to the vertical shaft for sliding movement to any desired position in locking or unlocking position at the desired position, making it possible to hold the head of the subject in the vertical position relative to the ground plane or in the horizontal position or any desired tilted position.

The stimulating apparatus is provided, in which said shoulder restrainer includes shoulder arms and shoulder restraining brackets held by the arms at end portions thereof in adjustable manner and provided with shoulder pads for close contact with the shoulders of the subject. The stimulating apparatus is provided, in which said occipital region restrainer includes a vertical shaft mounted to the seat frame for vertical movement to take various vertical positions, a first clamp arm supported by the vertical shaft for vertical movement, a second clamp arm held by the first clamp arm for adjustable movements in any desired directions and for locking engagement at any desired position, and occipital region restraining brackets held by the second clamp arm for adjustable movements in any desired directions and for locking and unlocking engagement at any desired position. The stimulating apparatus is provided, in which said temple restrainer includes open-close arms, which are overlapped and mounted at one end portions to the second clamp arm in locking or unlocking state and in relatively sliding relationship at the overlapped one end portions, and temple pads held by temple arms fixed to the other ends of the open-close arms.

According to another implementation of the present invention, in methods for stimulating otolith organs by linear acceleration to cause complementary eye movements, there is provided a method for stimulating otolith organs by linear acceleration, comprising the steps of: tilting left and right otolith organs of a subject from the head's horizontal plane in the Reid stereotaxic coordinate system; applying linear acceleration to the head of the subject in the tilted position; and applying different linear acceleration stimuli derived from the linear acceleration to left and right otolith organs, respectively.

The stimulating method is provided, in which, for functional testing the otolith organs, the head is tilted on one side down 10 degrees from the head's horizontal plane in the Reid stereotaxic coordinate system, and, during applying the linear acceleration, the truncus of the subject is fixed to a stimulating apparatus with the shoulders, occipital region and temples fixedly restrained relative to the stimulating apparatus during functional testing the otolith organs.

PREFERRED IMPLEMENTATION OF THE PRESENT INVENTION

Referring next to the accompanying drawings, embodiments of an apparatus and a method for stimulating otolith organs according to the present invention are described. It should be noted that the present invention is not limited to the illustrated embodiments.

The stimulating method according to the present invention belongs to methods for stimulating otolith organs by linear acceleration to cause complementary eye movements, and it comprises the steps of: tilting otolith organs on one side of a subject from the head's horizontal plane in the Reid stereotaxic coordinate system; applying linear acceleration to the head of the subject in the tilted position; and applying different linear acceleration stimuli derived from the linear acceleration to left and right otolith organs, respectively. Applying different stimuli to left and right utriculi or sacculi, respectively, makes it possible to measure individual functions of the left and right otolith organs.

The stimulating apparatus capable for carrying out the stimulating method for applying different stimuli to the left and right utriculi or sacculi, comprises: a base section with a source of linear acceleration, a revolving section supported by the base section for linear reciprocal movements, a tilting section supported by the revolving section to tilt from the head's horizontal plane in the Reid stereotaxic coordinate system, a seat section supported by the tilting section, and a restraining section, on the seat section, adjustable in all directions to restrain a subject with respect to the seat section. In brief, the base section A, revolving section B, tilting section C, seat section D and restraining section E constitute five major sections.

The base section A is placed on the ground plane G and has arranged thereon a strut, which the revolving section B is arranged about for revolution through 360 degrees. Arranged on the revolution section B is the tilting section C, which can be tilted with respect to the ground plane G at most through 90 degrees. Mounted to the tilting section C is the seat section D. The seat section D includes a seat back and a step, which can take the vertical position or horizontal position. Mounted to the above-mentioned seat section D is the restraining section E. The restraining section E is adjustable in any desired directions and can be locked and unlocked. This restraining section E is composed of a shoulder restrainer for restraining the shoulders of a subject, an occipital region restrainer for restraining the occipital region of the subject and a temple restrainer for restraining temples of the subject.

The sections A to E are described in detail below.

Figure 5:
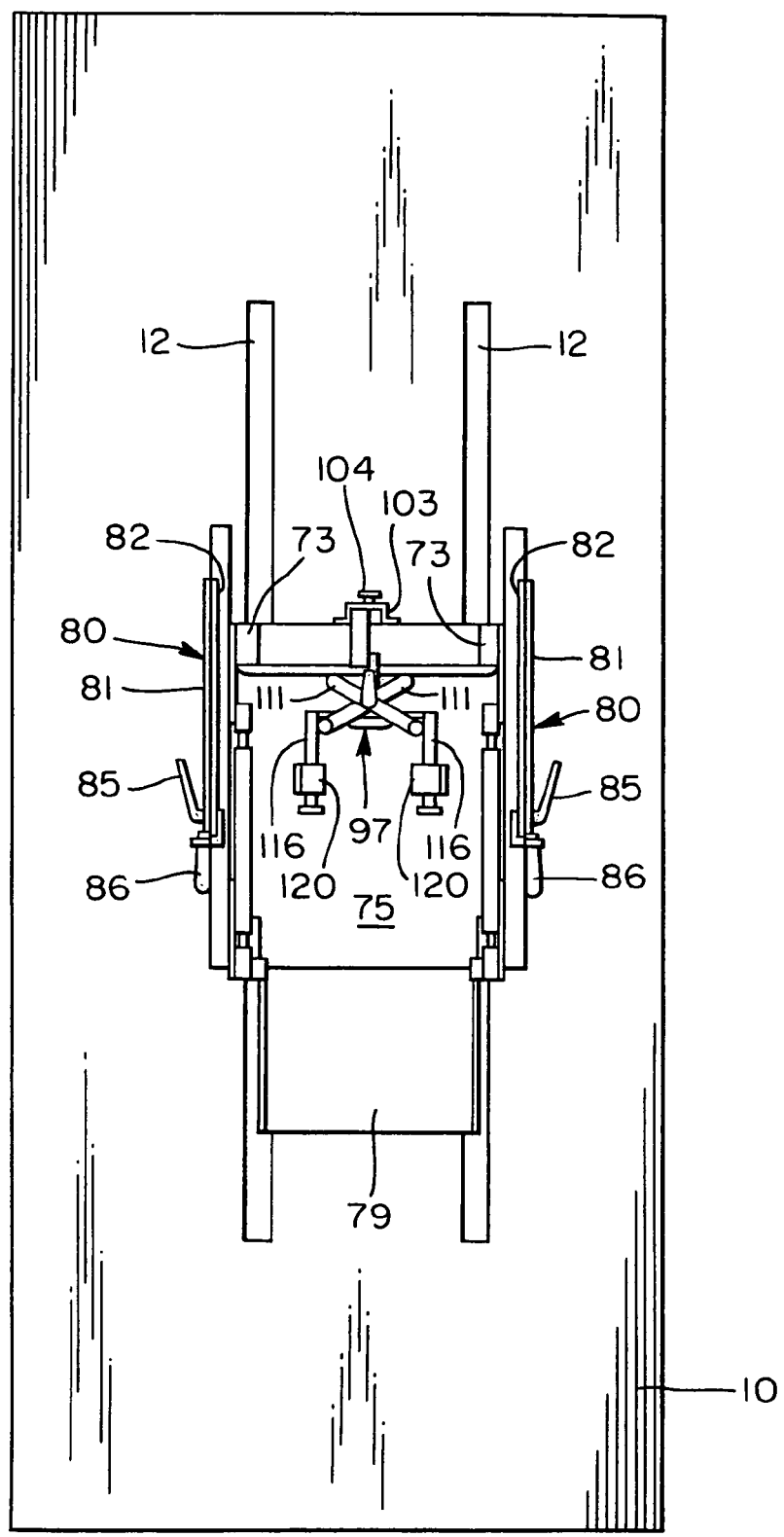
FIG. 5 is a plan view, viewing FIG. 2 from the upper side, illustrating the major portion of the stimulating apparatus according to the present invention.
Figure 6:
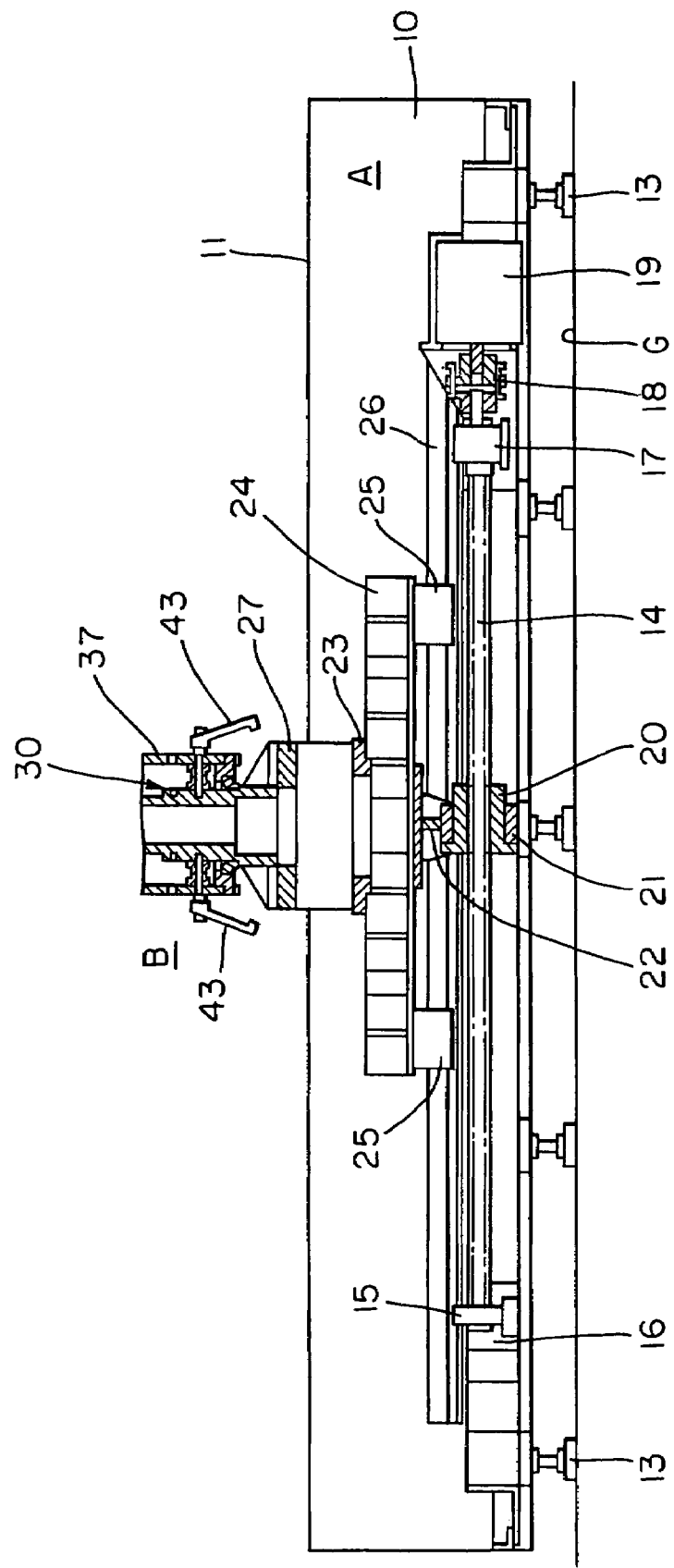
FIG. 6 is a view illustrating the inner structure of a base section of the stimulating apparatus according to the present invention by removing unnecessary parts to show fragmentary section of a coupling region of a driving force transmitting system of a source of linear acceleration with a revolving section.

Base Section A:

As shown in FIGS. 2-4 and 6, the base section A is placed on the ground plane G. The base section A includes a main cover 10 that is rectangular in plan view and recessed upwardly in transverse cross section. The main cover 10 has, on one side, a top board 11 formed with two parallel guide grooves 12, 12 (see FIGS. 2 and 5). The main cover 10 has an open end on the side opposite to the one side where the top board 11 lies. Fixed to the open end are leveling feet 13, 13, with which the base section A may be leveled horizontally with respect to the ground plane G using, for example, an appropriate leveling instrument. Within the above-mentioned main cover 10, a known ball screw 14 is supported longitudinally.

At one end, the ball screw 14 is supported by a bearing 15, which is fixed to a bracket 16 fixed to the main cover 10. At the other end, the ball screw 14 is supported by a bearing 17, which is fixed to a bracket fixed to the main body 10. Via a known servo flex coupling, the above-mentioned ball screw 14 is coupled to a source of linear acceleration in the form of a servo motor 19. Turning on a switch causes the servo motor 19 to rotate via the servo flex coupling 18 the ball screw 14, causing a known ball nut 20 engaged with the ball screw 14 to move linearly along the axis of the ball screw 14 to the left and right (see FIG. 6).

Fixed to the above-mentioned ball nut 20 is a nut block 21, which nut block 21 is fixed via a slide block key base 22 to a slide block base 23. The slide block base 23 is fixed to a frame 24, which frame 24 has slides 25, 25 fixed thereto at both end portions. The slides 25, 25 are guided along a linear guide rail 26 for sliding movement relative thereto. The linear guide rail 26 is fixed to the main cover 10 for allowing left-right linear movements of the frame 24 in response to the linear movements of said ball nut 20. These linear movements cause the corresponding left-right linear movements of a slide side board 27 fixed to the housing fixed frame 24 along the guide grooves 12, 12 of the main cover 10.

Figure 2:
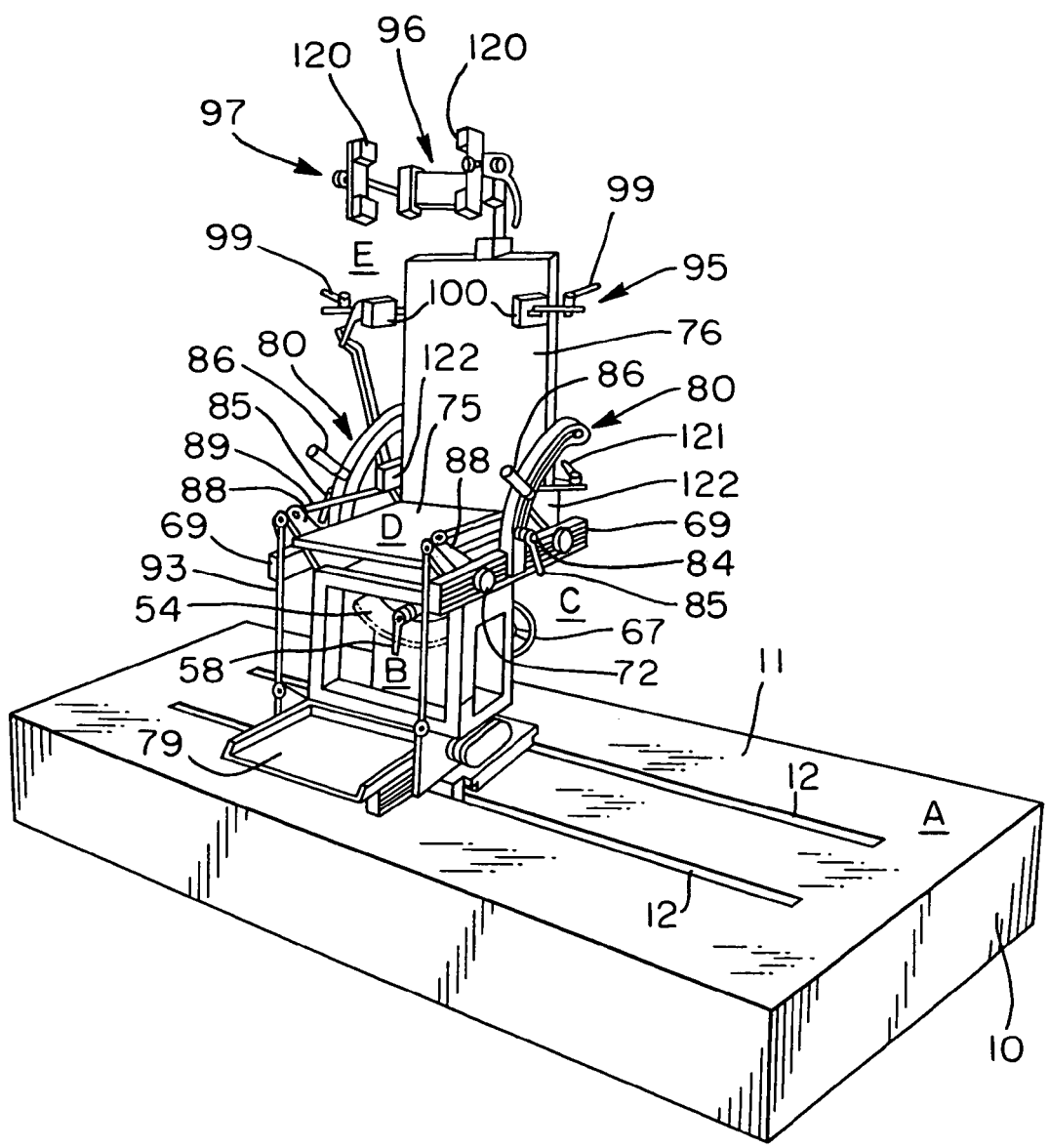
FIG. 2 is a perspective view illustrating the overall of an apparatus for stimulating otolith organs by linear acceleration, according to the present invention, with a seat in vertical position with respect to the ground plane.
Figure 3:
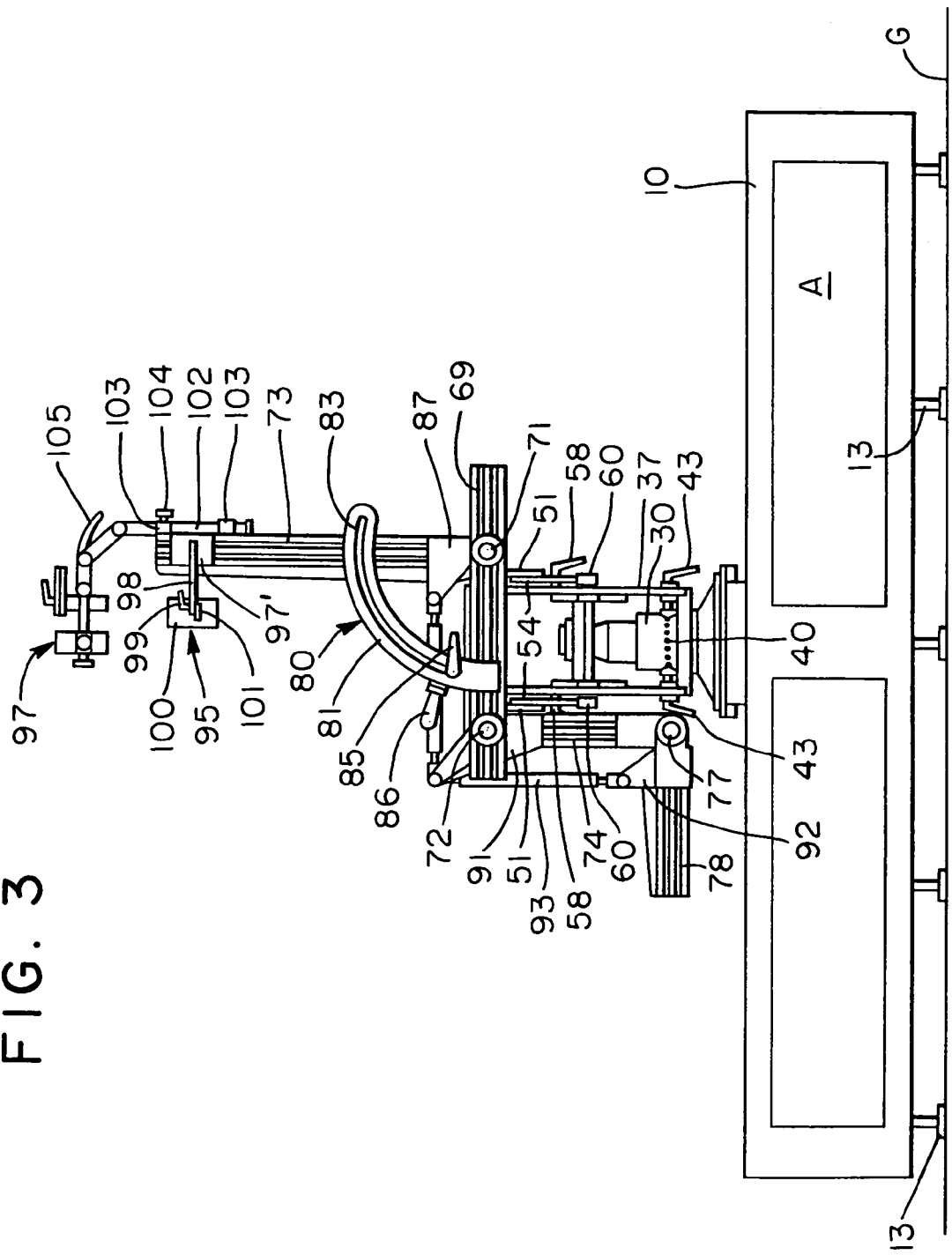
FIG. 3 is a side view, viewing FIG. 2 from the right-hand side, illustrating a major portion of the stimulating apparatus according to the present invention.
Figure 4:
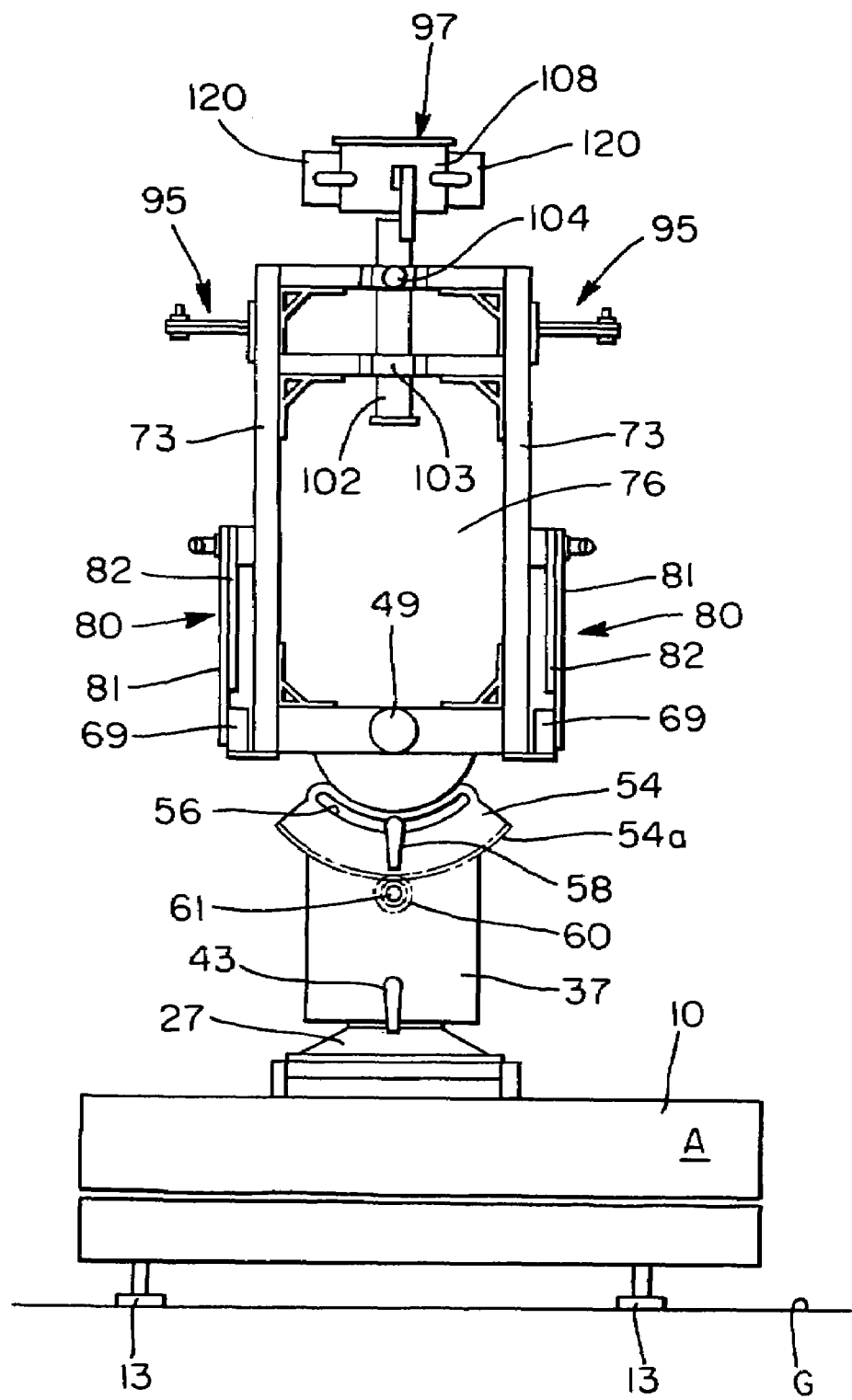
FIG. 4 is a rear view, viewing FIG. 2 from the rear side, illustrating the major portion of the stimulating apparatus according to the present invention.
Figure 7:
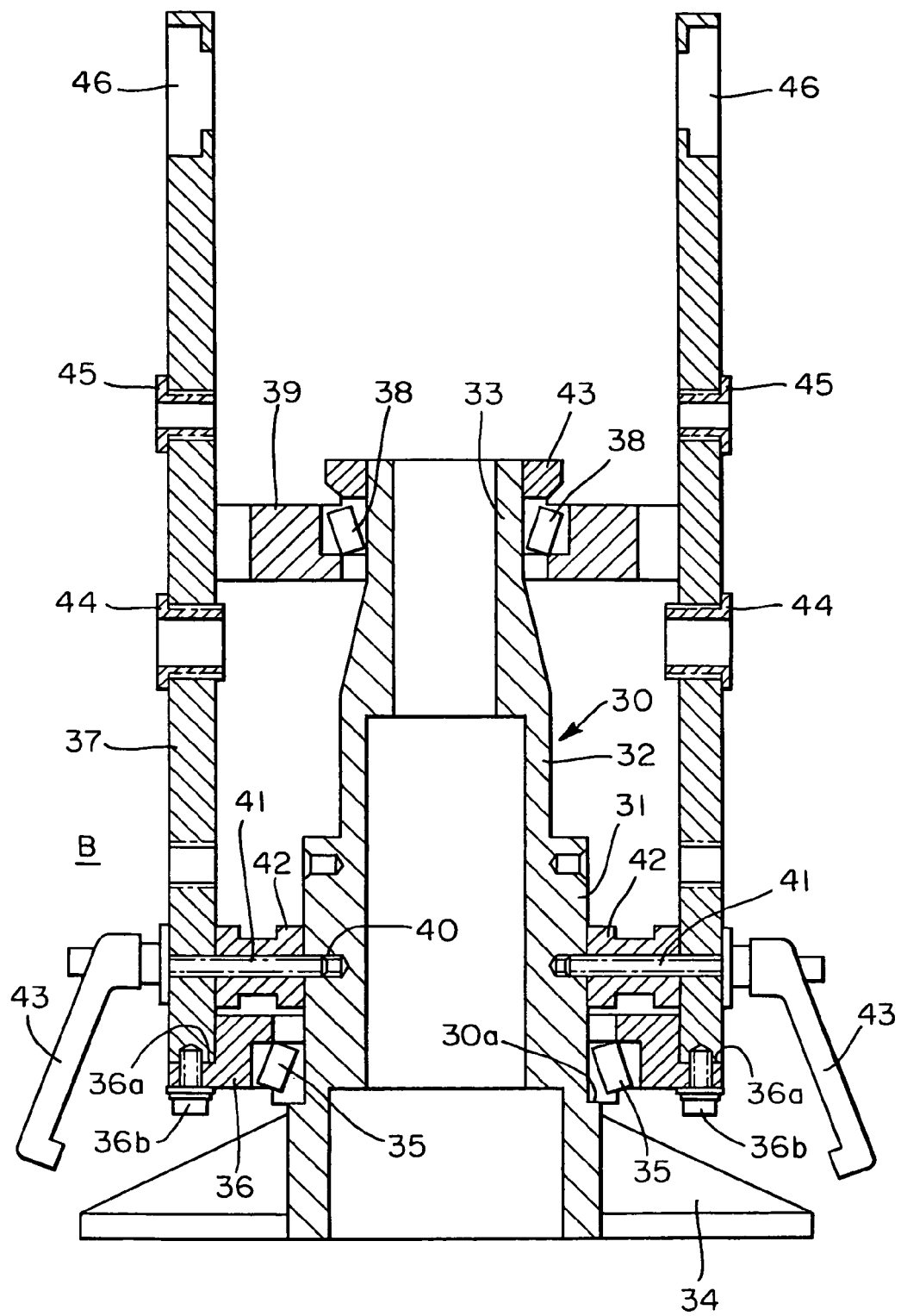
FIG. 7 is an enlarged section cut vertically through the revolving section of the stimulating apparatus according to the present invention.

Revolving Section B:

The revolving section B is shown in FIGS. 2, 3, and 7. The revolving section B is provided with a strut 30, which has an almost tubular overall configuration. The strut 30 has an enlarged diameter lower tube section 31, a slightly reduced diameter middle tube section 32 and a further reduced diameter upper tube section 33 connected continuously one after another in this order, and it is hollowed for weight reduction. At a lower end, the lower tube section 31 has fixed thereto a coupling bracket 34, which is fixed to the slide side board 27 of said base section A by bolts and nuts (see FIGS. 3, 4 and 6).

Along its outer surface, the lower tube section 31 is formed with an annular step 30a. On the annular step 30a, the lower tube section 31 is equipped with a known rotary mechanism composed of taper rollers 35 and a lower taper roller bearing 36. Along its outer surface, the lower taper roller bearing 36 is formed with a step 36a for supporting a frame 37. Supporting the frame 37 with its lower end placed on the step 36a, the frame 37 is fixed to the step 36a by screwing blind bolts 36b into the frame 37 from a lower end surface of the lower taper roller bearing 36. Along its outer surface, the upper tube section 33 is equipped with a known rotary mechanism composed of taper rollers 38 and an upper taper roller bearing 39. The upper taper roller bearing 39 is fixed to the frame 37. In this manner, with the lower rotary mechanism 35, 36 and the upper rotary mechanism 38, 39, the frame 37 is supported for revolution about the strut 30 through 360 degrees. The upper rotary mechanism 38, 39 is fixed to the upper tube section 33 by screwing a nut 43 into engagement with an end portion thereof.

Drilled inwardly from the outer surface of the lower tube section 31 are adjustment bores 40, 40, which are angularly spaced one after another by, for example, 5 to 15 degrees, for adjusting angular position of the frame 37 (see FIG. 3). The adjustment bores 40 are provided for determining an angular position and locking the frame 37 to the determined angular position. The adjustment bores 40 allow insertion of known diametrically opposed clamp pins 41, 41 when the determined angular position is accomplished. The clamp pins 41, 41 are operated from outside of the frame 37 by known clamp levers 43, 43. The clamp pins 41, 41 are inserted into the adjustment bores 40, 40 via a metal fitting for brake 42. Operating the clamp levers 43, 43 cause the pins 41, 41 to clamp the lower tube section 31 via the metal fitting for brake 42 or to release it from the clamped state. In order to support the tilting section C, the frame 37 is equipped with tilted axis bearings 44 and nuts 45, and, at its upper end, it is formed with mounting recesses 46.

Figure 8:
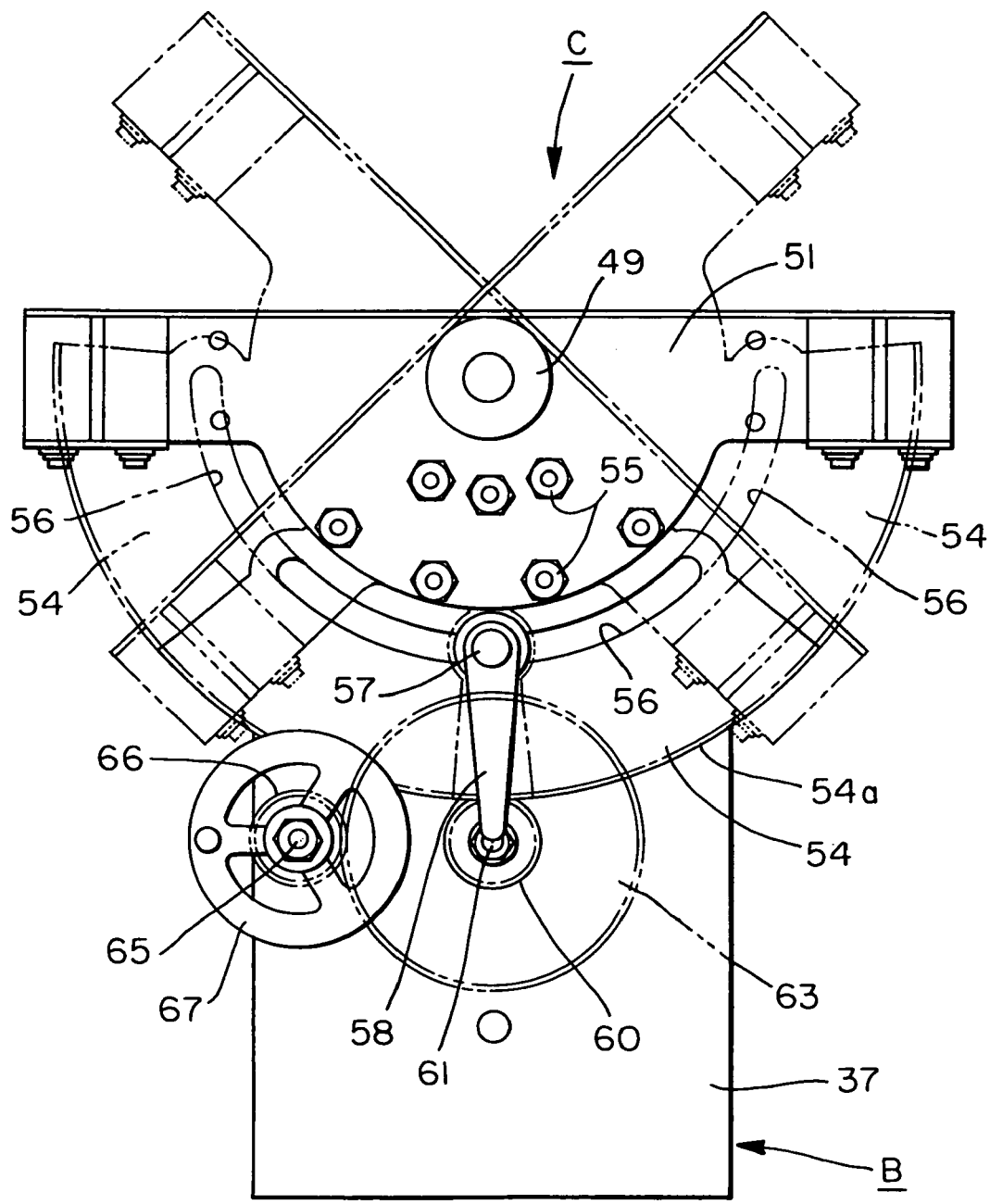
FIG. 8 is an enlarged view, viewing a tilting section of the stimulating apparatus according to the present invention from the rear side in FIG. 2.
Figure 9:
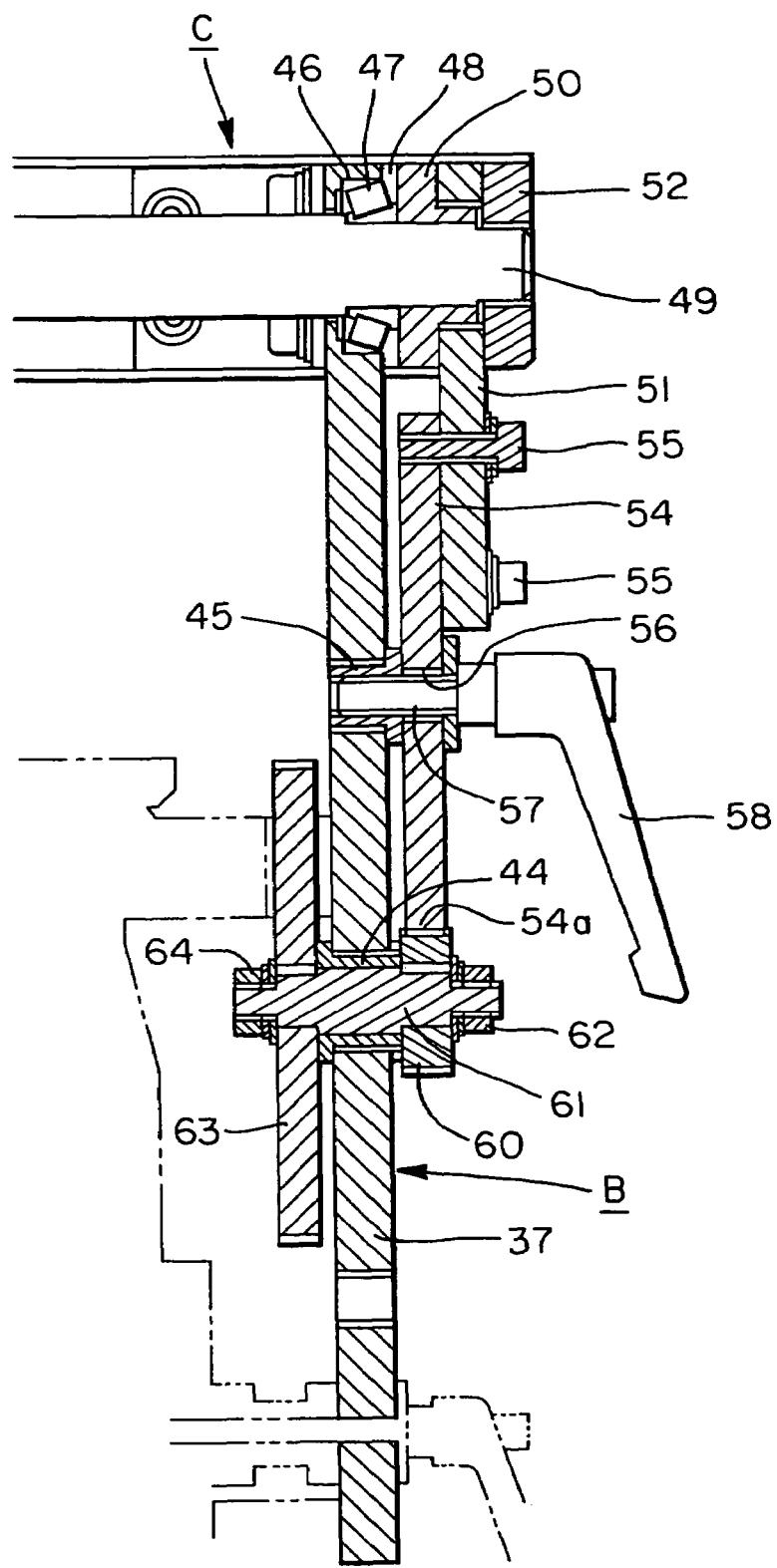
FIG. 9 is an enlarged view of a tilting mechanism for controlling the tilting section of the stimulating apparatus according to the present invention, illustrating, in section, one of transmission mechanisms, only.

Tilting Section C:

The tilting section (tilting means) C is shown generally in FIGS. 2 and 3, and specifically in FIGS. 8 and 9. For tilting the tilting section C, a pair of transmission gearing mechanisms is arranged at angularly distant positions spaced through 180 degrees although only one of them is shown in the Figures. The tilting section C is supported on the revolving section B so that it can tilt 45 degrees at most with respect to the ground plane G. At the mounting recesses 46, 46, the frame 37 is equipped with known rotary mechanisms, only one being shown in FIG. 9 and composed of taper rollers 47 and a taper roller bearing 48. The rotary mechanisms 47, 48 support a main shaft 49 (an axis about which the tilting section C can rotate) of the tilting section C. At both ends, the main shaft 49 has fixed thereto two flanges, only one being shown in FIG. 7 at 50. These flanges 50 are fixed to gear mount plates 51 (see FIG. 3), respectively. The gear mount plates 51, 51 are fixed to end portions of the main shaft 49 by screwing nuts 52 into engagement with the end portions, respectively. With the rotary mechanisms 47, 48, the main shaft 49, flanges 50 and gear mount plates 51 are allowed to tilt as a unit using the frame 37 as a fulcrum. This movement allows the tilting section C to tilt with respect to the frame 37 through desired degrees, allowing it to tilt with respect to the head's horizontal plane in the Reid stereotaxic coordinate system through desired degrees, which degrees are determined in response to the object of examination. The tilting section C supports frames 53, 53, which, in turn, support the seat section D.

Each of the plates 51 has a radial protrusion at a mid portion between its both ends (see FIG. 8). The radial protrusion of each plate 51 has fixed thereto a segment gear 54 (see FIG. 3) by means of a plurality of bolts 55. The segment gear 54 is formed with a circular guide groove 56, which receives a clamp pin 57 of a known clamp mechanism. At its leading end portion, each clamp pin 57 is inserted into the mating one of the nuts 45 fixed to the frame 37. Operating clamp levers 58, 58 of the clamp mechanism cause the pins 57 to clamp the sector gears 54 or to release it from the clamped state. Accordingly, when the object of examination determines an angle to be selected, an operator moves the clamp levers 58 to release the clamped states of the clamp mechanisms, respectively, and rotates the main shaft 49 rotated through the selected angle with the help of a preset protractor or scale.

Each of the segment gears 54 has its external teeth 54a in meshing engagement with a pinion 60 on a pinion shaft 61. At its one end, the pinion shaft 61 supports the pinion 60. The pinion shaft 61 extends through one of the bearings 44 fixed to the frame 37 and supported thereby. The pinion 60 is coupled to the opinion shaft at the above-mentioned one end and fixed thereto by means of a nut 62. A spur gear 63 is coupled to the other end of the pinion shaft 61 and fixed thereto by a nut 64. As mentioned before, another transmission gearing mechanism that is identical in structure to that described above is arranged at angularly distant position spaced through 180° from the latter. The spur gear 63 is in meshing engagement with a pinion 66 coupled to one end of a pinion shaft 65 (see FIG. 8). Another pinion, not shown, identical in structure to the pinion 66, is coupled to the other end of the pinion shaft 65, and it is in meshing engagement with another spur gear, not shown, identical in structure to the spur gear 63.

The pinion shaft 65 is supported on the frame 37 for rotation, and it is fixedly coupled to a handle 67 (see FIG. 8). With this handle 67, the operator can rotate the pinion shaft 65. This rotation of the pinion shaft 65 causes the spur gears, one being shown at 63 and the other not shown, to rotate the pinions, one being shown at 60 and the other not shown, thereby imparting equal driving forces via the opposite transmission gearing mechanisms to the tilting section E for smooth tilting movement thereof.

Figure 10:
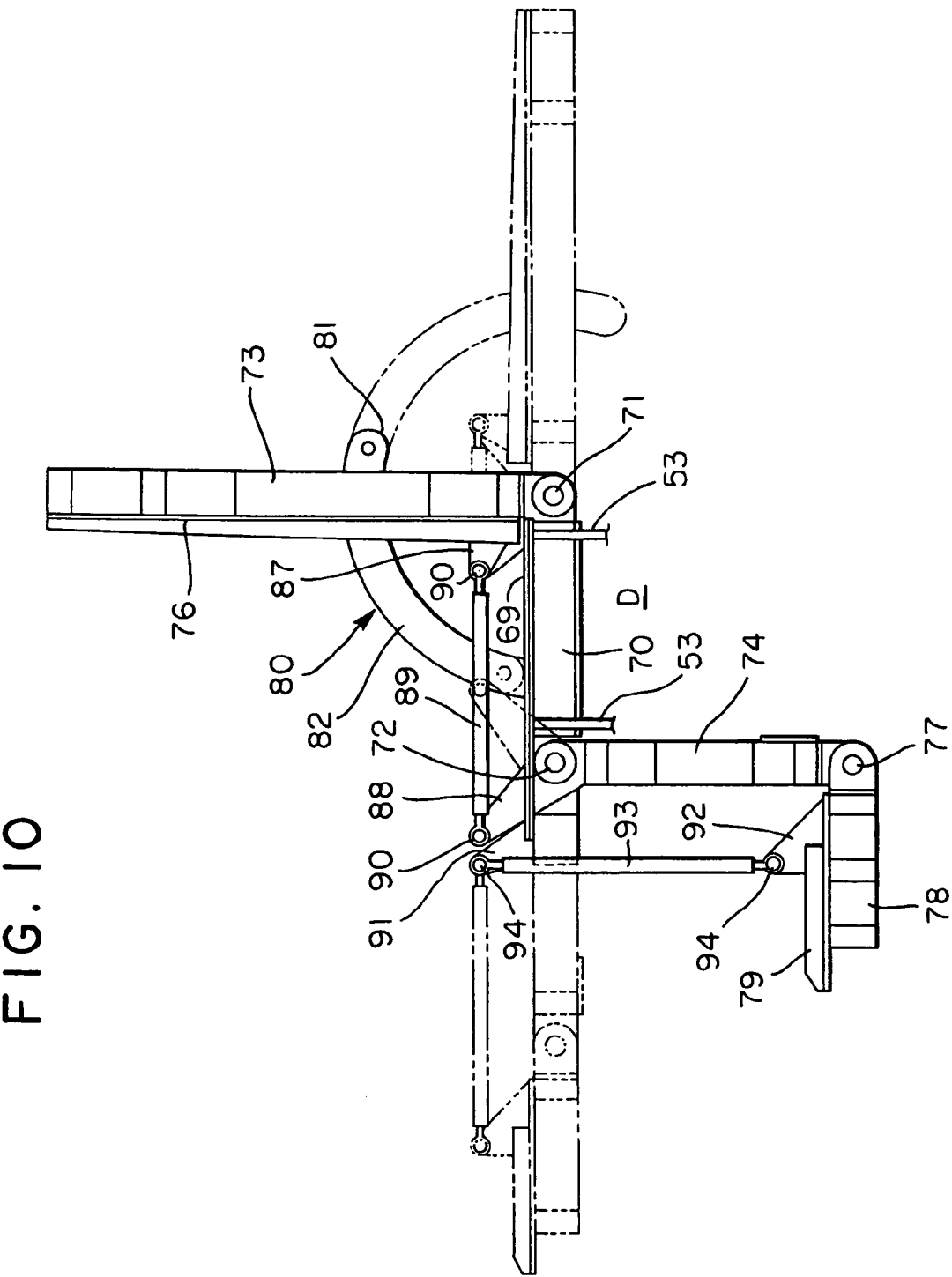
FIG. 10 is an enlarged side view of a seat section of the stimulating apparatus according to the present invention, illustrating in the fully drawn line the seat section in the vertical position with respect to the ground plane and in the two-dots chain line the horizontal position with respect to the ground plane.
Figure 11:
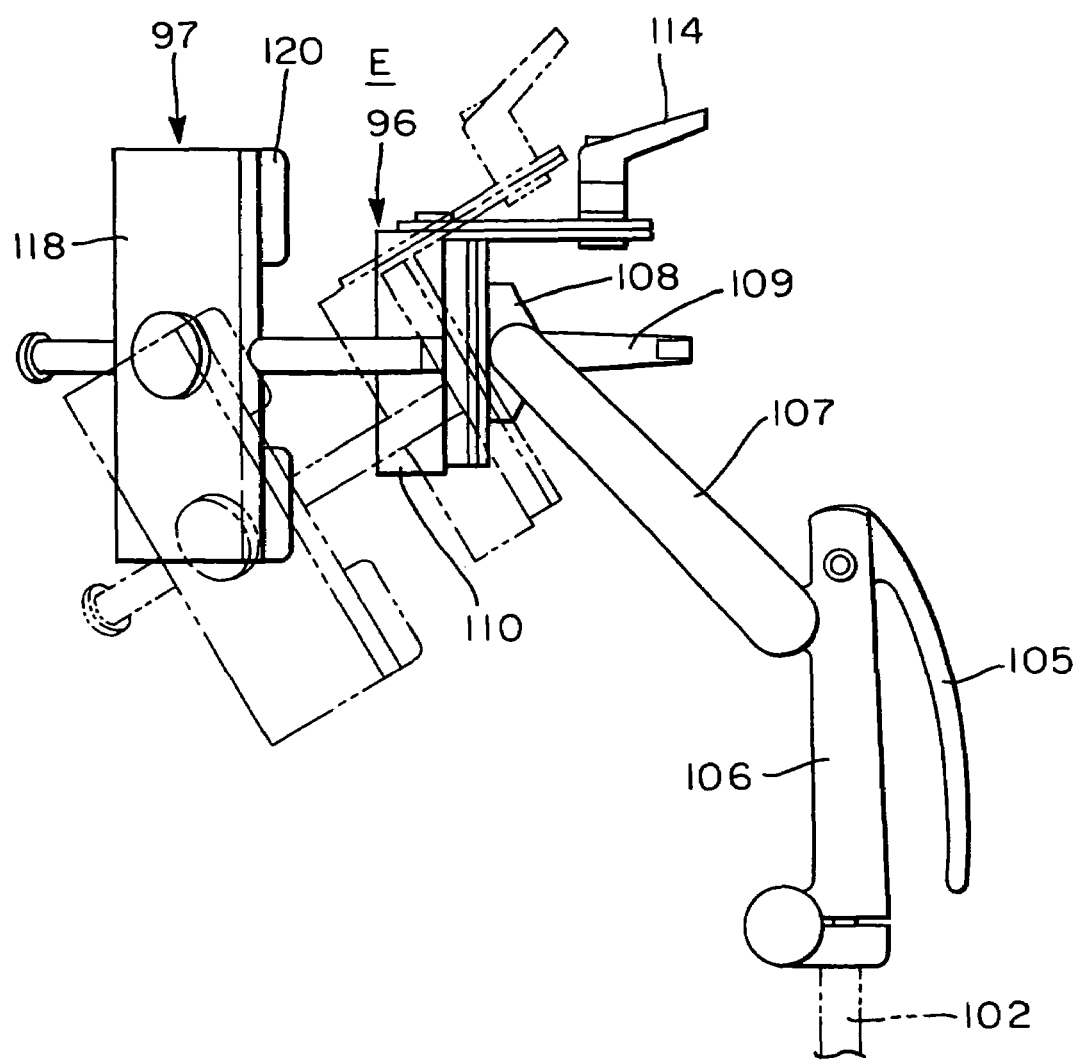
FIG. 11 is an enlarged view of a restraining section of the stimulating apparatus according to the present invention, illustrating in the fully drawn line and in the two-dots chain line finely adjusted positions of an occipital region restrainer and a temple restrainer.
Figure 12:
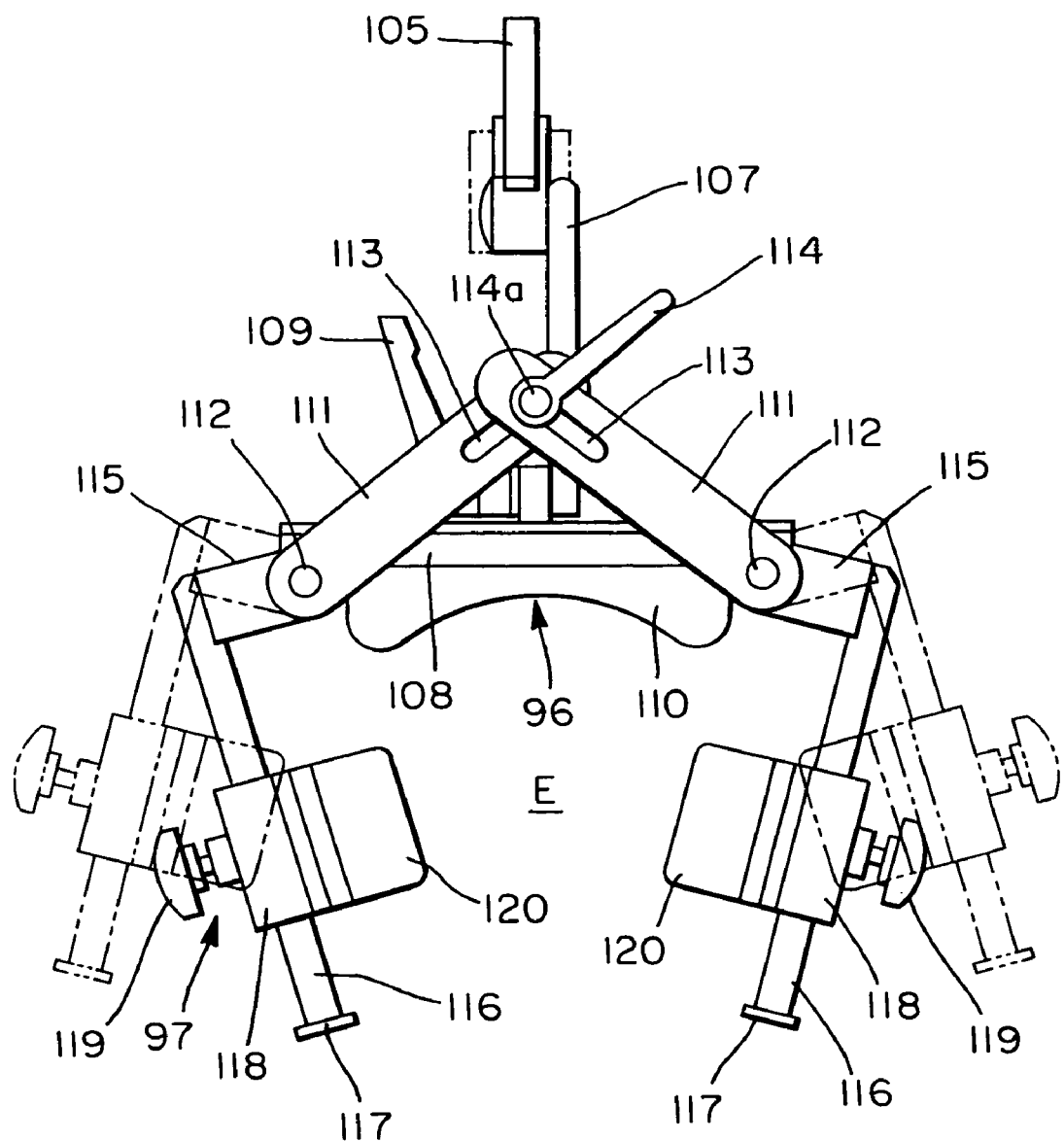
FIG. 12 is an enlarged plan view of the restraining section of the stimulating apparatus according to the present invention, illustrating in the fully drawn line and in the two-dots chain line finely adjusted positions of the temple restrainer.

Seat Section D:

The seat section D is shown in FIGS. 2, 3 and 10. The seat section D is equipped with a pair of parallel rectangle-shaped seat frames 69, 69 (see FIG. 2). Fixed to the mutually facing side surfaces of the seat frames 69, 69 are frames 70 (only one being shown), respectively. Each of the frames 70 are fixed to the frames 53, 53 supported by the revolving section C in the parallel position with respect to the ground plane G. The seat section D is composed of seat frames 69, seat-back frames 73, step supporting frames 74 and step frames 78, which are interlinked.

At one end, each of the seat frames 69, 69 has a seat-back rotary shaft 71, while, at the other end, it has a step rotary shaft 72. The rotary shaft 71 rotatably support one ends of the seat-back frames 73, 73. Arranged between the seat frames 69, 69 is a seat sheet 75 (see FIG. 2). Arranged between the seat-back frames 72, 72 is a seat-back sheet 76 (see FIG. 10) for supporting the back of the seated subject. The step rotary shaft 72 rotatably supports upper ends of the step supporting frames 74, 74. At lower ends, the step supporting 74, 74 rotatably support one ends of the step frames 78, 78, respectively. The step frames 78, 78 have fixed thereto a step 79.

Fixed to outer sides of the seat frames are curved guide mechanisms 80, 80 (see FIGS. 2, 3 and 10), respectively. The guide mechanisms 80, 80 guide a conjoint action of the seat-back frames 73, 73 and step supporting frames 74, 74 during displacement of them between the vertical and horizontal states, with respect to the ground plane G. When the step supporting frames 74, 74 are in the vertical state with respect to the ground plane G, the step frames 78 assume the horizontal state with respect to the ground plane G. When the step supporting frames 74, 74 are in the horizontal state with respect to the ground plane G, the step frames 78, 78 are displaced into the same horizontal state.

The guide mechanisms 80, 80 are composed of outer guide plates 81, 81 (see FIGS. 2, 3 and 4) and inner guide plates 82, 82 (see FIG. 10). The inner guide plates 82, 82 are allowed to move along the outer guide plates 81, 81 in sliding engagement therewith, respectively. At one ends, the outer guide plates 81, 81 are fixed to the seat frames 69, 69, respectively (see FIGS. 2 and 3). The other ends of the outer guide plates 81, 81 project beyond the seat back 76 when the seat back 76 is in the vertical position (see FIGS. 2 and 10). The outer guide plates 81, 81 and the inner guide plates 82, 82 are symmetric in shape, allowing the inner guide plates 82, 82 to move circularly in the outer guide plates 81, 81, respectively, until they project from the terminal ends of the outer guide plate 81, 81 during displacement of the seat back 76 from the vertical position to the horizontal position. In this manner, the outer guide plates 81, 81 and the inner guide plates 82, 82 cooperate with other to bring the seat-back frames 73, 73 into the horizontal state with respect to the ground plane G (see FIG. 10). At the same time, they bring the step supporting frames 74, 74 and the step frames 78, 78 into the same horizontal state with respect to the ground plane G (see FIG. 10).

The opposite outer guide plates 81, 81 are formed with curved guide grooves 83, 83, respectively (see FIG. 3). The guide grooves 83, 83 receive clamp pins 84 of known clamp mechanisms to allow movement of the clamp pins. At one ends, the clamp pins 84 are connected to the inner guide plates 82, and, at the opposite ends, they are connected to clamp levers 85, 85, respectively. The clamp levers 85, 85 project outwardly of the outer guide plates 81, 81, respectively. Operating the clamp levers 85, 85 brings the inner guide plates 82, 82 into the clamped state or releases the clamped state. At one ends, the inner guide plates 82, 82 has grips 86, 86, respectively. At the other free ends, the inner guide plates 82, 82 are associated with, the seat-back frames 73, 73, respectively. Accordingly, after releasing the clamped state by the clamp mechanisms, sliding the grips 86, 86 along the outer guide plates 81, 81 causes the seat-back frames 73, 73 to shift from the vertical position to the horizontal position or vice versa. The grips 86, 86 are arranged within the reach of the seated subject.

At one and opposite ends, the seat-back rotary shaft 71 rotatably supports one ends of brackets 87, 87. At one and opposite ends, the step rotary shaft 72 rotatably supports one ends of brackets 88, 88. The brackets 87, 87 and their mating brackets 88, 88 are interconnected by coupling rods 89, 89 via shafts 90, 90, one shaft 90 rotatably linking one ends of the coupling rods 89, 89 with the brackets 87, 87, the other shaft 90 rotatably linking the opposite ends of the coupling rods 89, 89 with the brackets 88, 88. There are brackets 91, 91 fixed to the seat frames 69, 69, respectively, and brackets 92, 92 fixed to the step frames 78, 78, respectively. The brackets 91, 91 and their mating brackets 92, 92 are interconnected by coupling rods 93, 93 via shafts 94, 94, one shaft 94 rotatably linking one ends of the coupling rods 93, 93 with the brackets 91, 91, the other shaft 94 rotatably linking the opposite ends of the coupling rods 93, 93 with the brackets 92, 92. Using the seat-back rotary shaft 71 and the step rotary shaft 72 as fulcrum points, moving the brackets 87, 87, 88, 88 and coupling rods 89, 89 to the right, viewing in FIG. 10 displace the seat-back frames 73, 73 from the state illustrated by the fully drawn line to the state illustrated by the two-dots chain line accompanied by displacement of the step supporting frames 74, 74 and step frames 78, 78 from the state illustrated by the fully drawn line to the state illustrated by the two-dots chain line. Returning the brackets 87, 87, 88, 88 and the coupling rods to the left, viewing in FIG. 10, causes displacement of the seat-back frames 73, 73 from the state illustrated by the two-dots chain line to the state illustrated by the fully drawn line and displacement of the step supporting frames 74, 74 and step frames 78, 78 from the state illustrated by the two-dots chain line to the state illustrated by the fully drawn line.

Restraining Section E:

The restraining section E is shown in FIGS. 2, 3, 11 and 12. The restraining section E includes a shoulder restrainer 95 for restraining shoulders of the seated subject (see FIGS. 2 and 3), an occipital region restrainer 96 for restraining an occipital region of the subject, and a temple restrainer 97 for restraining temples of the subject. The shoulder restrainer 95 is so positioned as to be near the both shoulders of the subject on the seat sheet 75. The shoulder restrainer 95 includes arms 98, 98. At one ends, the arms 98, 98 are fixed to brackets 97, 97, which are fixed to the seat-back frames 73, 73. At the other ends, the arms 98, 98 have shoulder arms 101, 101, which are adjustable to various positions by manipulating known clamp mechanisms provided with clamp levers 99, 99. The shoulder arms 101, 101 have shoulder pads 100, 100. Operating the clamp levers 99, 99 bring the shoulder arms 101, 101 into the clamped state or release the clamped state, allowing the fine adjustment of the shoulder pads 100, 100 into close contact with the shoulders of the subject.

The occipital region restrainer 96 and temple restrainer 97 has a vertical shaft 102 in common. With this vertical shaft 102, they are supported on the seat-back frames 73, 73. The seat-back frames 73, 73 have fixed thereto guide metal fittings 103, 103. The guide metal fittings 103, 103, which are fixed to a desired position on the seat-back frames 73, 73 by means of screw 104 (see FIGS. 3 and 4), guide the vertical shaft 102 for vertical movements. The vertical shaft 102 supports a first clamp arm 106, which in turn supports a second clamp arm 107. Operating a clamp lever 105 of a known clamp mechanism brings the first and second clamp arms 106 and 107 into clamped state or releases the clamped state. When released from the clamped state by the clamp lever 105, the first and second clamp arms 106 and 107 can carry out fine adjustment in a direction toward the head of the subject and in the vertical directions. Held on the second clamp arm 107 via a known clamp mechanism with a clamp lever 109 is a mount bracket 108. Operating the clamp lever 109 to release the clamped state by the clamp mechanism allows fine adjustment of an occipital pad 110 into close contact with the occipital region of the subject.

At one ends, open-close arm plates 111, 111 are held via pivots 112, 112 on both ends of the mount bracket 108. At the other end portions, the open-close arm plates 111, 111 are overlapped. At these overlapped end portions, the open-close arm plates 111, 111 are formed with elongate openings 113, 113. These elongate openings 113, 113 intersect. At the intersecting point, a clamp pin 114*a* of a known clamp mechanism is inserted into the elongate openings 113, 113. Operating a clamp lever 114 of the clamp mechanism brings the open-close arm plates 111, 111 into clamped state or releases the clamped state. When clamped by the clamp lever 114, the open-close arm plates 111, 111 are locked. When the clamped state is released, the open-close arm plates 111, 111 can rotate about the pivots 112, 112.

Fixed to the open-close arm plates 111, 111 are one ends of brackets 115, 115, respectively. At the other ends, the brackets 115, 115 are fixed to one ends of temple arms 116, 116, respectively. At the other ends, the temple arms 116, 116 have stops 117, 117, respectively. Held on the temple arms 116, 116 are temple holders 118, 118 provided with lock dials 119, 119. When released by the lock dials 119, 119, the temple holders 118, 118 can slide along the temple arms 116, 116, respectively. The temple holders 118, 118 have fixed thereto temple pads 120, 120, respectively. These temple pads 120, 120 are brought into close contact with temples of the head of the subject. Operating the clamp lever 114 of the clamp mechanism to release the clamped state of the open-close arm plates 111, 111 allows fine adjustment in a direction from the position illustrated by the two-dots chain line in FIG. 12 toward the position illustrated by the fully drawn line or in the opposite direction. With regard to the seat section D again, the seat section D is provided with waist-support pads 112, 112 (see FIG. 2). The waist-support pads 112, 112 are clamped or released from the clamped state by operating clamp levers 121.

Next, it is explained how to carry out functional tests of otolith organs using the stimulating apparatus according to the present invention.

First of all, the base section A is placed on the ground plane G within a horizontal plane. Placing the base section within the horizontal plane with respect to the ground plane G is carried out by adjusting the leveling feet 12 with reference to a leveling instrument. With reference to FIG. 2, the seat sheet 75, the seat-back sheet 76, and the step 79 are placed in the illustrated position by placing the seat sheet 75 in the horizontal position parallel to the ground plane G, the seat-back sheet 76 in the vertical position relative to the seat sheet 75 and the step 79 in the horizontal position.

Next, a subject is seated on the seat sheet 75 with its back on the seat-back sheet 76 and its feet on the step 79. The waist-support pads 122, 122 are used to embrace the lumber of the subject from the sides to hold the lumber stationary relative to the seat sheet 75. The shoulders of the subject are held stationary by a restraining band (not illustrated) provided on the seat-back sheet 76. Further, ankles of the subject are held stationary relative to the step 79 by a restraining band (not illustrated) provided on the step 79. Furthermore, the shoulder restrainer 95, the occipital region restrainer 96 and the temple restrainer 97, securely restrain the shoulders, the occipital region and the temples of the subject, respectively.

In order to restrain the shoulders by the shoulder restrainer 95, with the clamp levers 99, 99, the clamp mechanisms are released, allowing fine adjustment of the shoulder arm plates 111, 111 to bring the shoulder pads 100, 100 into close contact with the them in a manner to interpose them. Then, the shoulders are restrained or held stationary by clamping the clamping mechanism. Subsequently, in order to restrain the occipital region of the subject, the clamp lever 105 is operated to release the clamp mechanism, allowing adjustment to move the first clamp arm 106 and the second clamp arm 107 upward and downward and/or forward and backward to bring the occipital region pad 110 into opposed relationship to the occipital region. When the occipital region pad 110 is opposed to the occipital region, the clamp lever 105 is operated to clamp the first and second clamp arms 106 and 107 again. Next, the clamp lever 109 is operated to release the clamped state due to the clamp mechanism, allowing fine adjustment to move the mount bracket 108 upward and downward and/or leftward and rightward and/or forward and backward to bring the occipital region pad 110 into close contact with the occipital region. When the occipital region pad 110 is in close contact with the occipital region, the clamp lever 109 is operated to accomplish the clamped state again, restraining or hold stationary the occipital region. Subsequently, in order to restrain temples of the subject, the clamp levers 114, 114 are operated to release the clamped state by the clamp mechanism, allowing the overlapped end portions of the intersecting open-close arm plates 111, 111 to slide relative to each other. This relative sliding movement causes displacement of the temple arms 116, 116 from the state illustrated by the fully drawn line in FIG. 12 to the state illustrated by the two-dots chain line or vice versa, bringing the temple pads 120, 120 into close contact with the temples of the subject. Then, the clamp lever 114 is operated to clamp the clamp mechanism to restrain or hold stationary temples.

As mentioned above, the head of the subject is securely held stationary by restraining the three regions, namely, the occipital region, the left temple and the right temple. Further, the chin of the subject is restrained or held stationary by a chin-restraining band (not shown) provided on the restraining section E. As the head of the subject is restrained or held stationary during the test, no substantial load is applied to collum (cervical vertebrae or muscularis of collum) when the head is subject to linear acceleration load.

Now, it is concretely explained how to carry out a functional test of utriculus on one side, for example, utricular macula of left ear or left utricular macula, of subjects.

Figure 1A:
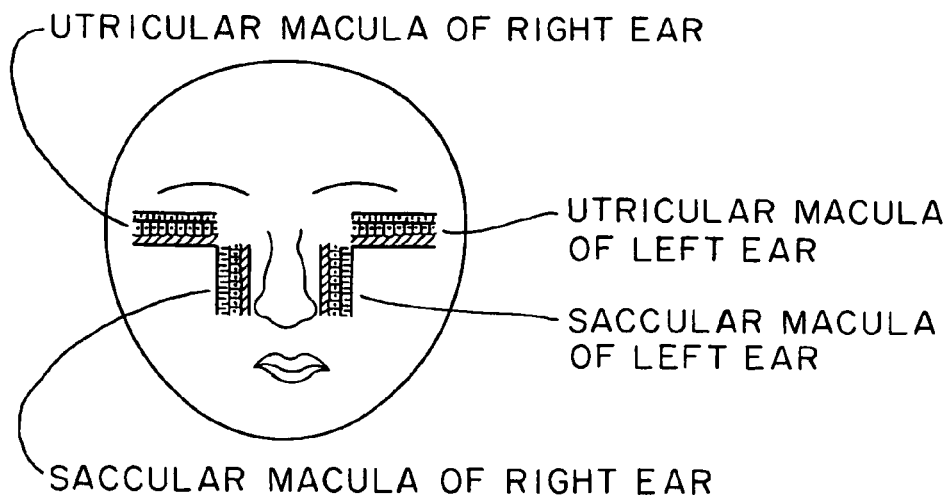
FIG. 1(A) is a view illustrating the relationship between left and right utricular maculae and left and right saccular maculae of otolith organs when the head of a human is in the normal position.
Figure 1B:
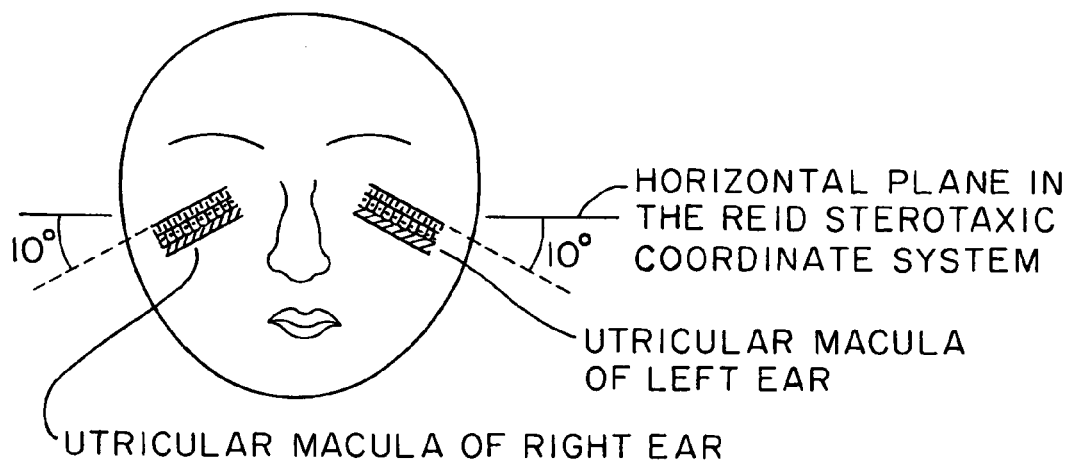
FIG. 1(B) is a view illustrating the left and right utricular maculae tilted down 10° from the head's horizontal plane in the Reid stereotaxic coordinate system when the head is in the normal position as illustrated in FIG. 1(C).
Figure 1C:
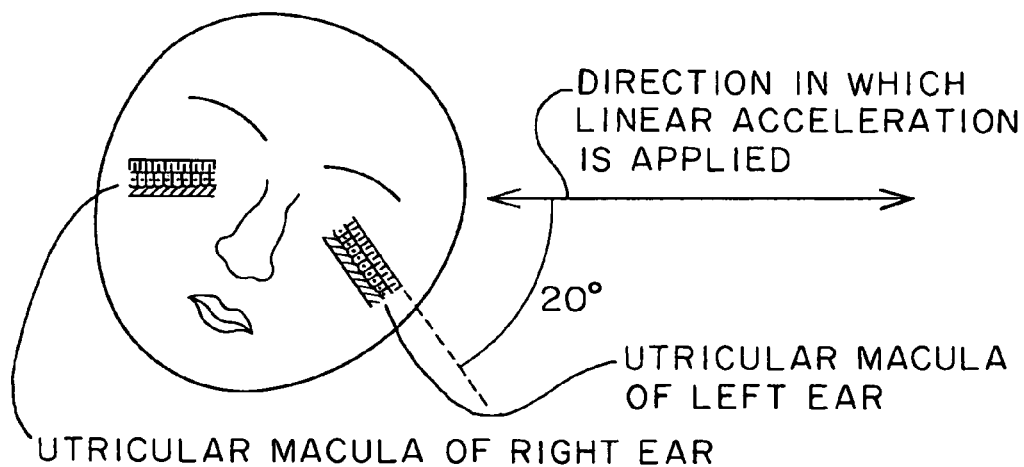
FIG. 1(C) is a view illustrating the relationship between the left and right utricular maculae when the head is in the tilted position with the left ear tilted down 10° from the horizontal plane shown in FIGS. 1(A) and 1(B).

Left and right utriculi of subject held stationary relative to the stimulating apparatus are conditioned as shown in FIG. 1(B). Left and right utricular maculae are tilted down 10 degrees from the head's horizontal plane in the Reid stereotaxic coordinate system. In order to bring the left utricular macula into the head's horizontal plane in the Reid stereotaxic coordinate system, the stimulating apparatus according to the present invention is tilted down leftward viewing in FIG. 2 by operating the clamp levers 58, 58 to release the clamped state due to the clamp mechanisms and rotating the handle 67 counterclockwise viewing in FIG. 8. This rotation of the handle 67 causes the pinions 66, 66 fixed to he pinion shaft 65 to rotate in the same counterclockwise direction. This rotation of the pinions 66, 66 causes the spur gears 63, 63 to rotate clockwise. The clockwise rotations of the spur gears 63, 63 cause the coaxial pinions 60, 60 to rotate in the same clockwise direction, imparting rotational drives to the segment gears 54, 54 via their teeth 54a, 54a, which the pinions 60, 60 are in meshing engagement with. Thus, the segment gears 54, 54 are driven to rotate clockwise viewing in FIG. 8.

The segment gears 54, 54 rotate the gear mount plates 51, 51, causing the main shaft 49 to rotate clockwise viewing in FIG. 8. A tilting angle through which the main shaft 49 rotates must be accurately adjusted to 10°. After completion of tilting, the clamp levers 58, 58 are operated to clamp the clamp mechanisms. This tilting movement of the stimulating apparatus according to the present invention brings the left utricular macula of the subject into the head's horizontal plane in the Reid stereotaxic coordinate system, and it tilts the right utricular macula down further by 10° to 20°.

Next, turning on the switch of the servo motor 19 causes the servo flex coupling 18 to rotate the ball screw 14. This rotation of the ball screw 14 causes the ball nut 20 to reciprocate along the longitudinal line. As the ball nut 20 drives the slide block key base 22 via the nut block 21, the reciprocate motion of the ball nut 20 causes the slide block key base 22 to reciprocate in left-right directions viewing in FIG. 6. The left-right reciprocating movements of the slide block key base 22 causes the slide block base 23 to reciprocate in left-right directions viewing in FIG. 6. This reciprocating movements of the slide block base 23 causes the frames 24, 24 guided by the linear guide rail 26 to reciprocate in the same manner, causing the slides 25, 25 fixed to the frames 24, 24 to reciprocate along the guide grooves 12, 12, causing the subject on the base section A to reciprocate.

In the position with an ear on one side tilted down 10 degrees, linear acceleration is applied directly to the head. In this tilted position, a utricular macula on the opposite side is disposed in the head's horizontal plane in the Reid stereotaxic coordinate system. Under this condition, this utricular macula directly receives the linear acceleration stimulus. This stimulus is of the non-attenuation characteristic. With electronystagram (ENG) or electrooculography (EOG) or three-dimensional analyzer using an infrared CCD camera, the compensatory eye movements due to this stimulus are measured.

With three different trials (1), (2) and (3) listed below, experiments were carried out to examine the function of utriculi with respect to the subject population consisted of 7 healthy adults.

(1) The subjects were seated and not tilted. Linear acceleration stimulus with 0.7 Hz in left-right directions and 0.25G at the maximum acceleration was applied.

(2) The subjects were seated and tilted right ear down 10 degrees. The same liner acceleration stimulus was applied.

(3) The subjects were seated and tilted left ear down 10 degrees. The same liner acceleration stimulus was applied.

Complementary eye movements were measured by EOG under these three conditions. The complementary eye movements are sinusoidal movements in left-right directions, whose amplitudes were measured as listed below.

Result of Amplitude

| Subjects | Sex | Age | Trial (1) Mean Amp. | Trial (2) Mean Amp. | Trial (3) Mean Amp. |
|---|---|---|---|---|---|
| 1 | Male | 48 | 3.76 deg. | 3.73 deg. | 3.08 deg |
| 2 | Male | 33 | 2.10 deg. | 1.14 deg. | 2.19 deg. |
| 3 | Female | 32 | 3.03 deg. | 3.28 deg. | 2.08 deg. |
| 4 | Female | 21 | 6.82 deg. | 3.50 deg. | 6.26 deg. |
| 5 | Male | 22 | 3.02 deg. | 3.51 deg. | 2.70 deg. |
| 6 | Male | 52 | 2.16 deg. | 2.41 deg. | 1.06 deg. |
| 7 | Female | 25 | 3.68 deg. | 1.65 deg. | 4.19 deg. |

With respect to the amplitudes of complementary eye movements due to trials (2) and (3), a bounded difference was found ($p < 0.01$).

According to trial (1), utriculi on both sides were stimulated. According to trials (2) and (3), different linear acceleration stimuli were applied to left and right ears. The present data clearly showed the existence of a bounded difference with respect to the amplitudes of complementary eye movements due to trials (2) and (3) of applying different stimuli. This result confirmed the report on an asymmetry in function between left and right otolith organs (Shirley G. DIAMOND, Charles H. MARKHAM: "Ocular torsion as a test of the asymmetry hypothesis of space motion sickness", Acta Astronaut July; 27: pp 11-17, 1992). A significant similarity in amount of amplitude between trail (1) and one of trials (2) and (3) with greater amplitude was observed. As a result, trials (2) and (3) can measure the function of utriculus within an ear on one side primarily.

In the preceding, different trials of stimulating utriculi were illustrated and explained. The present invention is not limited to them. Other examples are explained below.

Measurement of Sacculi:

Applying linear acceleration in different directions to the head makes it possible to stimulate sacculus primarily. Linear acceleration is applied to the head of subject lying down on one side in forward-backward directions relative to the head. Different linear acceleration stimuli can be applied to left and right sacculi by tilting the head of subject lying on one side one ear down 70 to 90 degrees.

Measurement of Vestibular Evoked Myogenic Potentials (VEMP):

Using the stimulating apparatus according to the present invention, application of linear acceleration stimulus with the frequency as high as 2 Hz at most can be applied to the head. Functional of otolith organs can be examined, without relying on measurement of complementary eye movements, by measuring myogenic potentials of musculus sternocleidmastoideus (sterno cleido mastoidmuscle: SCM, for example) and/or appendicular muscles (soleus muscle, for example) during stimulating the otolith organs and processing the measured data.

Measurement; where the Maculae of Utriculi and/or Sacculi Greatly Differ in Orientation:

In normal case, the utricular macula is tilted down about 10 degrees from the horizontal plate in the Reid stereotaxic coordinate system. If the utricular macula is tilted down less or greater than 10 degrees, the magnitude of linear acceleration should be varied or the tilted angle of the head should be varied.

INDUSTRIAL APPLICABILITY OF THE INVENTION

According to the present invention, it is now possible to apply different linear acceleration stimuli to left and right otolith organs, respectively, only by tiling the head of subject one ear down from the head's horizontal plane in the Reid stereotaxic coordinate system. Operation is simple in tilting the head from the head's horizontal plane in the Reid stereotaxic coordinate system during application of linear acceleration. With this stimulating method, independent functional tests of left and right otolith organs are possible. The present invention has a wide range of applicability in tests and examinations during clinical practice.

The present application claims the priority of Japanese Patent Application No. 2003-096938, filed Mar. 31, 2003, the disclosure of which is hereby incorporated by reference in its entirety.

What is claimed is:

1. An apparatus for stimulating otolith organs in a subject by linear acceleration, said apparatus comprising:
    (a) a base section with a source of linear acceleration;
    (b) a revolving section supported by the base section, said revolving section is slidably mounted on the base section and is coupled to the source of linear acceleration and is adapted to carry out reciprocal movements under action of the source of linear acceleration;
    (c) a tilting section supported by the revolving section to tilt from a head of the subject on one side down from the head's horizontal plane in a Reid stereotaxic coordinate system, wherein said tilting section includes a rotary main shaft, a pair of transmission gearing mechanisms cooperating with the rotary main shaft by way of gear mount plates, a handle for operating the transmission gearing mechanisms, and a mechanism to rotate the rotary main shaft by way of the transmission gearing mechanisms to a desired angular position using the handle in locking or unlocking position at the desired angular position;
    (d) a seat section supported by the tilting section; and
    (e) a restraining section, on the seat section, said restraining section includes an occipital region retainer and a temple retainer that are adjustable in an upward and downward direction and/or in a forward and backward direction, to restrain the subject with respect to the seat section;
    wherein said tilting section is configured to orient a subject's head relative to the source of linear acceleration such that different linear accelerations can be applied to left and right otolith organs, respectively, of the subject.

2. The apparatus as claimed in claim 1, wherein said base section includes a major cover, the major cover being formed with guide grooves at a top thereof, the major cover including, inside thereof, a reciprocal mechanism that performs reciprocal movements caused due to the source of linear acceleration, the reciprocal mechanism including slides guided by said guide grooves.

3. The apparatus as claimed in claim 1, wherein the revolving section includes a strut fixed to the base section and a frame supported, via a rotary mechanism, for revolution about the strut, and wherein the revolution of the support frame is operable from outside of the frame in locking or unlocking position at any desired angular position.

4. The apparatus as claimed in claim 1, wherein the seat section includes seat frames, seat-back frames rotatably connected to the seat frames, step supporting frames rotatably connected to the seat frames, and means for interlinking the seat frames, the seat back frames and the step supporting frames.

5. The apparatus as claimed in claim 4, wherein the seat section includes guide mechanisms on the seat frames, respectively, each guide mechanism including an outer guide plate and an inner guide plate in sliding engagement with the outer guide plate.

6. The apparatus as claimed in claim 5, wherein the restraining section includes a shoulder restrainer.

7. The apparatus as claimed in claim 6, wherein the shoulder restrainer includes shoulder arms and shoulder restraining brackets held by the shoulder arms at end portions thereof in adjustable manner and provided with shoulder pads for close contact with the shoulders of subject.

8. The apparatus as claimed in claim 6, wherein the occipital region retainer includes a vertical shaft fixedly supported relative to the seat frames, a first clamp arm vertically adjustable relative to the vertical shaft, a second clamp arm supported on the first clamp arm for adjustable movement to a first desired position in locking or unlocking state at the first desired position, and a mount bracket supported on the second clamp arm for adjustable movement to a second desired position in locking or unlocking state at the second desired position, and wherein said mount bracket has an occipital region pad.

9. The apparatus as claimed in claim 8, wherein the temple restrainer includes open-close arms, which are overlapped and mounted at one end portion to the second clamp arm in locking or unlocking state and in relatively sliding relationship at the overlapped one end portion, and temple pads held by temple arms fixed to the other ends of the open-close arms.

* * * * *